United States Patent
Sweeney et al.

(10) Patent No.: US 8,649,853 B2
(45) Date of Patent: Feb. 11, 2014

(54) CARDIAC FUNCTION MONITOR USING INFORMATION INDICATIVE OF LEAD MOTION

(75) Inventors: Robert J. Sweeney, Woodbury, MN (US); Allan C. Shuros, St. Paul, MN (US); Krzysztof Z. Siejko, Maple Grove, MN (US); David C. Olson, Eden Prairie, MN (US); Frank Ingle, Palo Alto, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 124 days.

(21) Appl. No.: 13/168,531

(22) Filed: Jun. 24, 2011

(65) Prior Publication Data

US 2011/0319778 A1      Dec. 29, 2011

Related U.S. Application Data

(60) Provisional application No. 61/359,430, filed on Jun. 29, 2010.

(51) Int. Cl.
| | |
|---|---|
| A61B 5/04 | (2006.01) |
| A61B 17/04 | (2006.01) |
| A61F 2/00 | (2006.01) |
| A61F 13/00 | (2006.01) |
| A61M 1/10 | (2006.01) |
| A61N 1/00 | (2006.01) |

(52) U.S. Cl.
USPC .............. 600/513; 623/3.1; 623/3.2; 623/3.3; 600/16; 600/37; 606/232; 607/18

(58) Field of Classification Search
USPC ......... 623/3.1–3.3; 600/16, 37, 513; 606/232; 607/18
See application file for complete search history.

(56) References Cited

U.S. PATENT DOCUMENTS

| 3,012,192 A | 12/1961 | Lion |
| 4,011,500 A | 3/1977 | Pelletier et al. |

(Continued)

FOREIGN PATENT DOCUMENTS

| EP | 0578748 B1 | 5/1996 |
| EP | 0670743 B1 | 12/2001 |

(Continued)

OTHER PUBLICATIONS

"U.S. Appl. No. 13/168,471, Response filed Jul. 2, 2013 to Restriction Requirement mailed Jun. 11, 2013", 8 pgs.

(Continued)

*Primary Examiner* — Niketa Patel
*Assistant Examiner* — Lindsey G Hankins
(74) *Attorney, Agent, or Firm* — Schwegman Lundberg & Woessner, P.A.

(57) ABSTRACT

Systems and methods to monitor cardiac function using information indicative of lead motion are described. In an example, a system including an implantable medical device can include a receiver circuit configured to be electrically coupled to conductor comprising a portion of an implantable lead and be configured to obtain information indicative of a movement of the implantable lead due at least in part to a motion of a heart. The system can include a sensing circuit configured to obtain information indicative of cardiac electrical activity. The system can include a processor circuit configured to construct a template representative of a contraction of the heart, where the template can be constructed using the information indicative of the movement of the implantable lead due at least in part to the motion of the heart during the contraction, and using the information indicative of the cardiac electrical activity sensed during the contraction.

22 Claims, 18 Drawing Sheets

(56) References Cited

U.S. PATENT DOCUMENTS

| | | | |
|---|---|---|---|
| 5,197,467 A | 3/1993 | Steinhaus et al. | |
| 5,271,392 A | 12/1993 | Ferek-Petric | |
| 5,324,326 A | 6/1994 | Lubin | |
| 5,361,776 A | 11/1994 | Samuelson et al. | |
| 5,417,717 A | 5/1995 | Salo et al. | |
| 5,448,222 A | 9/1995 | Harman | |
| 5,554,177 A | 9/1996 | Kieval et al. | |
| 5,564,434 A | 10/1996 | Halperin et al. | |
| 5,693,074 A | 12/1997 | Ferek-Petric | |
| 5,694,943 A | 12/1997 | Brewer et al. | |
| 5,897,577 A | 4/1999 | Cinbis et al. | |
| 5,899,927 A | 5/1999 | Ecker et al. | |
| 6,094,981 A | 8/2000 | Hochstein | |
| 6,285,898 B1 | 9/2001 | Ben-Haim | |
| 6,317,628 B1 | 11/2001 | Linder et al. | |
| 6,445,951 B1 | 9/2002 | Mouchawar | |
| 6,591,143 B1 | 7/2003 | Ekwall | |
| 6,731,973 B2 * | 5/2004 | Voith | 600/513 |
| 6,869,404 B2 | 3/2005 | Schulhauser et al. | |
| 6,873,870 B2 | 3/2005 | Ferek-Petric | |
| 6,980,866 B2 | 12/2005 | Yu et al. | |
| 7,025,727 B2 | 4/2006 | Brockway et al. | |
| 7,035,684 B2 | 4/2006 | Lee | |
| 7,047,083 B2 | 5/2006 | Gunderson et al. | |
| 7,248,923 B2 | 7/2007 | Maile et al. | |
| 7,689,286 B2 | 3/2010 | Pastore et al. | |
| 7,787,946 B2 | 8/2010 | Stahman | |
| 8,478,392 B2 | 7/2013 | Sweeney et al. | |
| 2005/0137636 A1 | 6/2005 | Gunderson et al. | |
| 2006/0282000 A1 | 12/2006 | Zhang et al. | |
| 2007/0299477 A1 | 12/2007 | Kleckner et al. | |
| 2008/0077333 A1 | 3/2008 | Maxey et al. | |
| 2008/0119750 A1 | 5/2008 | Patangay et al. | |
| 2008/0242976 A1 | 10/2008 | Robertson et al. | |
| 2008/0269820 A1 | 10/2008 | Nilsson | |
| 2008/0294217 A1 * | 11/2008 | Lian et al. | 607/28 |
| 2009/0030334 A1 | 1/2009 | Anderson et al. | |
| 2009/0177110 A1 | 7/2009 | Lyden et al. | |
| 2009/0204163 A1 | 8/2009 | Shuros et al. | |
| 2009/0299432 A1 | 12/2009 | Stadler et al. | |
| 2010/0069768 A1 | 3/2010 | Min et al. | |
| 2010/0076279 A1 | 3/2010 | Shuros et al. | |
| 2010/0179421 A1 | 7/2010 | Tupin | |
| 2011/0319772 A1 | 12/2011 | Ingle | |
| 2011/0319776 A1 | 12/2011 | Sweeney et al. | |
| 2011/0319779 A1 | 12/2011 | Sweeney et al. | |
| 2011/0319782 A1 | 12/2011 | Sweeney et al. | |

FOREIGN PATENT DOCUMENTS

| | | |
|---|---|---|
| EP | 1469910 B1 | 12/2006 |
| EP | 1515770 B1 | 6/2009 |
| WO | WO-9503086 A2 | 2/1995 |
| WO | WO-9527531 A1 | 10/1995 |
| WO | WO-2004103458 A2 | 12/2004 |
| WO | WO-2005089638 A1 | 9/2005 |
| WO | WO-2008054261 A1 | 5/2008 |
| WO | WO-2009058638 A1 | 5/2009 |
| WO | WO-2010033190 A2 | 3/2010 |
| WO | WO-2012005985 A2 | 1/2012 |
| WO | WO-2012005985 A3 | 1/2012 |
| WO | WO-2012005987 A2 | 1/2012 |
| WO | WO-2012005987 A3 | 1/2012 |
| WO | WO-2012005988 A2 | 1/2012 |
| WO | WO-2012005988 A3 | 1/2012 |
| WO | WO-2012005989 A2 | 1/2012 |
| WO | WO-2012005989 A3 | 1/2012 |
| WO | WO-2012005991 A2 | 1/2012 |
| WO | WO-2012005991 A3 | 1/2012 |

OTHER PUBLICATIONS

"U.S. Appl. No. 13/168,471, Restriction Requirement mailed Jun. 11, 2013", 5 pgs.

"U.S. Appl. No. 13/168,481 , Response filed Feb. 19, 2013 to Non Final Office Action mailed Nov. 19, 2012", 11 pgs.

"U.S. Appl. No. 13/168,481, Examiner Interview Summary mailed Feb. 26, 2013", 3 pgs.

"U.S. Appl. No. 13/168,481, Non Final Office Action mailed Nov. 19, 2012", 5 pgs.

"U.S. Appl. No. 13/168,481, Notice of Allowance mailed Mar. 5, 2013", 5 pgs.

"U.S. Appl. No. 13/168,507 , Response filed Mar. 21, 2013 to Non Final Office Action mailed Dec. 21, 2012", 14 pgs.

"U.S. Appl. No. 13/168,507, Final Office Action mailed Jul. 19, 2013", 11 pgs.

"U.S. Appl. No. 13/168,507, Non Final Office Action mailed Dec. 21, 2012", 10 pgs.

"U.S. Appl. No. 13/168,547 , Response filed Apr. 11, 2013 to Non Final Office Action mailed Dec. 11, 2012", 11 pgs.

"U.S. Appl. No. 13/168,547, Non Final Office Action mailed Dec. 11, 2012", 10 pgs.

"U.S. Appl. No. 13/168,547, Notice of Allowance mailed Apr. 30, 2013", 8 pgs.

"International Application Serial. No. PCT/US2011/041834, International Preliminary Report on Patentability mailed Jan. 17, 2013", 7 pgs.

"International Application Serial No. PCT/US2011/041834, International Search Report mailed Jan. 26, 2012", 3 pgs.

"International Application Serial No. PCT/US2011/041834, International Written Opinion mailed Jan. 26, 2012", 5 pgs.

"International Application Serial No. PCT/US2011/041850, International Preliminary Report on Patentability mailed Jan. 17, 2013", 7 pgs.

"International Application Serial No. PCT/US2011/041850, International Search Report mailed Feb. 1, 2012", 4 pgs.

"International Application Serial No. PCT/US2011/041850, International Written Opinion mailed Feb. 1, 2012", 5 pgs.

"International Application Serial No. PCT/US2011/041854, International Preliminary Report on Patentability mailed Jan. 17, 2013", 6 pgs.

"International Application Serial No. PCT/US2011/041854, International Search Report Mailed Jan. 26, 2012", 4 pgs.

"International Application Serial No. PCT/US2011/041854, International Written Opinion Mailed Jan. 26, 2012", 4 pgs.

"International Application Serial No. PCT/US2011/041860, International Preliminary Report on Patentability mailed Jan. 17, 2013", 7 pgs.

"International Application Serial No. PCT/US2011/041868, International Preliminary Report on Patentability mailed Jan. 17, 2013", 7 pgs.

"International Application Serial No. PCT/US2011/041868, International Search Report mailed Jan. 26, 2012", 4 pgs.

"International Application Serial No. PCT/US2011/041868, International Written Opinion mailed Jan. 26, 2012", 5 pgs.

"International Serial No. PCT/US2011/041860, International Search Report Jan. 26, 2012", 4 pgs.

"International Serial No. PCT/US2011/041860, International Written Opinion mailed Jan. 26, 2012", 5 pgs.

"Japanese Name Application Serial No. [Pending], Voluntary Amendment filed Dec. 27, 2012", With English Claims, 49 pgs.

"Lion's Twin-T Circuit Revisited", IEEE Engineering in Medicine and Biology, (Sep. 1992), 61-66.

Brusich, Sandro, et al., "Cardiac Lead Used as Contractility Sensor: Animal Study", HRS 2011, Innovators Poster Session—Esplanade Foyer Moscone South, (May 6, 2011), 7 pgs.

\* cited by examiner

CARDIAC FUNCTION MONITOR USING INFORMATION INDICATIVE OF LEAD MOTION

CLAIM OF PRIORITY

This patent application claims the benefit of priority, under 35 U.S.C. Section 119(e), to Ingle U.S. Provisional Patent Application Ser. No. 61/359,430, entitled "Lead Motion Sensing Using Cable Microphonics," filed on Jun. 29, 2010, which is hereby incorporated by reference herein in its entirety.

CROSS REFERENCE TO RELATED APPLICATIONS

This patent application is related to:
(1) U.S. patent application Ser. No. 13/168,481, now U.S. Pat. No. 8,478,392;
(2) U.S. patent application Ser. No. 13/168,507, published as U.S. 2011/0319776; and
(3) U.S. patent application Ser. No. 13/168,547, published as U.S. 2011/0319782; each of which is hereby incorporated herein by reference in its respective entirety.

BACKGROUND

An ambulatory medical device, such as an implantable medical device (IMD), can be configured for implant in a subject, such as a patient. An IMD can be configured to be coupled to a patient's heart such as via one or more implantable leads. Such an IMD can obtain diagnostic information or generate therapy to be provided to the patient, such as via the coupled implantable lead. Examples of such devices can include cardiac function management (CFM) devices including one or more of implantable pacemakers, implantable cardioverter-defibrillators (ICDs), cardiac resynchronization therapy devices (CRTs), or one or more other devices. Such devices can include one or more electrodes coupled, such as via the implantable lead, to circuitry located on or within the IMD. Such circuitry can be configured to monitor electrical activity, such as to obtain information indicative of electrical activity of the heart.

A cardiac electrotherapy device to measure cardiac contractions using an elongated lead body that forms a high frequency transmission line is mentioned in U.S. Pat. No. 5,693,074 entitled "Cardiac Electrotherapy Device for Cardiac Contraction Measurement."

A time domain reflectometry impedance sensor for measuring body impedance along a lead or catheter implanted in a patient's cardiovascular system is mentioned in U.S. Pat. No. 5,361,776 entitled "Time Domain Reflectometer Impedance Sensor Method of Use and Implantable Cardiac Stimulator Using Same."

Overview

Generally, an IMD can obtain information indicative of cardiac activity such as by monitoring cardiac electrical signals. For example, such events can include heart chamber contractions such as corresponding to electrical depolarization or repolarization of cells in cardiac muscle tissue. In an example, the IMD can determine indications of the subject's cardiovascular health such as using electrical signals obtained by a sensing circuit configured to obtain physiologic information (e.g., a blood pressure, a thoracic impedance indicative of respiration or fluid accumulation status, etc.). By obtaining such information, the IMD can monitor the effectiveness of a therapy (e.g., a pacing therapy, a cardiac resynchronization therapy, etc.), detect a change in cardiovascular health (e.g., detecting myocardial ischemia, stroke volume, or cardiac output), or detect lead dislodgement.

In an example, the IMD can obtain electrical signals, such as an intracardiac electrogram to monitor the effectiveness of a delivered therapy. For example, an IMD can estimate whether a delivered electrostimulation pulse evoked a contractile response in cardiac tissue (e.g., "capturing" the cardiac tissue). For example, electrical depolarization information obtained from the monitored cardiac electrical signals can be used such as to detect whether a corresponding muscle contraction was evoked. However, such evoked response detection techniques can have limitations. A variety of issues can prevent detection of an evoked response using cardiac electrical activity, such as the presence of noise, myopotentials unrelated to cardiac contraction, beat-to-beat variation in signal morphology or amplitude, or other factors.

Cardiac electrical activity can be sensed for other purposes, such as for detection of fusion (e.g., detection of a simultaneous or near-simultaneous occurrence of an intrinsic contraction slightly before or during delivery of electrostimulation). In one approach, a QRS-width can be estimated using sensed cardiac electrical information. But, such an approach can have limitations, as a diseased heart may exhibit abnormal electrical activity confounding such analysis based exclusively on sensed electrical activity.

Systems and methods to monitor cardiac function using information indicative of lead motion are described. In an example, a system including an implantable medical device can include a receiver circuit configured to be electrically coupled to conductor comprising a portion of an implantable lead and be configured to obtain information indicative of a movement of the implantable lead due at least in part to a motion of a heart. The system can include a sensing circuit configured to obtain information indicative of cardiac electrical activity. The system can include a processor circuit configured to construct a template representative of a contraction of the heart. Such templates can be constructed using the information indicative of the movement of the implantable lead due at least in part to the motion of the heart during the contraction, and using the information indicative of the cardiac electrical activity sensed during the contraction.

Example 1 can include subject matter (such as a system, a method, a means for performing acts, or a machine-readable medium including instructions that, when performed by the machine, cause the machine to perform acts, etc.) that can include an implantable medical device (IMD) that can include a receiver circuit, configured to be electrically coupled to a conductor comprising a portion of an implantable lead, the receiver circuit configured to obtain information indicative of a movement of the implantable lead due at least in part to a motion of a heart, a sensing circuit configured to obtain information indicative of cardiac electrical activity, and a processor circuit configured to construct a template representative of a contraction of the heart, the template constructed using the information indicative of the movement of the implantable lead due at least in part to the motion of the heart during the contraction, and using the information indicative of cardiac electrical activity sensed during the contraction.

In Example 2, the subject matter of Example 1 can optionally be configured such that the processor circuit can construct a composite template using information about multiple contractions.

In Example 3, the subject matter of Examples 1 and 2 can optionally be configured such that the processor circuit can construct the template at least in part via relating the information indicative of the motion of the implantable lead sampled during a specified interval of time to cardiac electrical activity information sampled during a similar interval of time, wherein the template is a two-dimensional template.

In Example 4, the subject matter of one or any combination of Examples 1-3 can optionally be configured such that the processor circuit can determine a contraction metric using the two-dimensional template.

In Example 5 the subject matter of one or any combination of Examples 1-4 can optionally be configured such that the processor circuit can determine the contraction metric via estimating an area enclosed by a shape formed by plotting the information indicative of the movement of the implantable lead received during the contraction with respect to the information indicative of cardiac electrical activity sensed during the contraction.

In Example 6, the subject matter of one or any combination of Examples 1-5 can optionally be configured such that the processor circuit can determine the contraction metric via estimating a spatial central tendency of a shape formed by plotting the information indicative of the movement of the implantable lead received during the contraction with respect to the information indicative of cardiac electrical activity sensed during the contraction.

In Example 7, the subject matter of one or any combination of Examples 1-6 can optionally be configured such that the processor circuit can determine the contraction metric via estimating a spatial dispersion between a first template corresponding to a first cardiac contraction and a second template corresponding to a second cardiac contraction.

In Example 8, the subject matter of one or any combination of Examples 1-7 can optionally be configured to include an implantable lead configured to be located within or near the heart, wherein the implantable lead can include a piezoelectric acoustic transducer configured to receive acoustic information indicative of the movement of the implantable lead, the piezoelectric acoustic transducer coupled to the conductor included in the implantable lead.

In Example 9, the subject matter of one or any combination of Examples 1-8 can optionally include an excitation circuit configured to provide a non-tissue stimulating, non-therapeutic electrical excitation signal to the implantable lead, the signal comprising a time-varying signal including a first range of frequencies.

In Example 10, the subject matter of one or any combination of Examples 1-9 can optionally be configured such that the information indicative of the movement of the implantable lead can include one or more of magnitude information, or phase information, corresponding to one or more frequencies included in the first range of frequencies, wherein the magnitude information, or phase information, can be determined at least in part using an electrical response signal provided by the implantable lead in response to the excitation signal and the movement of the implantable lead.

In Example 11, the subject matter of one or any combination of Examples 1-10 can optionally be configured such that one or more of the magnitude information, or the phase information, includes a time-varying portion corresponding to the movement of the implantable lead.

In Example 12, the subject matter of one or any combination of Examples 1-11 can optionally be configured such that the IMD includes the processor circuit.

In Example 13, the subject matter of one or any combination of Examples 1-12 can optionally be configured to include the implantable lead including the conductor, the implantable lead configured to be located within or near the heart, In Example 14, the subject matter of one or any combination of Examples 1-13 can optionally be configured such that the conductor can include one or more of a cardiac therapy delivery conductor or a cardiac electrical activity sensing conductor, wherein the conductor can be coupled to an implantable electrode included as a portion of the implantable lead.

In Example 15, the subject matter of Example 13 can optionally include a first lead located within or near a first location of the heart and a second lead located within or near a second location of the heart.

Example 16 can include, or can be combined with the subject matter of one or any combination of Examples 1-15 to optionally include, subject matter (such as an apparatus, a method, a means for performing acts, or a machine-readable medium including instructions that, when performed by the machine, cause the machine to obtain information indicative of the movement of an implantable lead, the lead including a conductor electrically coupled to a receiver circuit, the receiver circuit included as a portion of an implantable medical device (IMD), and the movement due at least in part to a motion of a heart, to obtain information indicative of cardiac electrical activity using a sensing circuit, and to construct a template representative of a contraction of the heart, the template constructed using information indicative of the movement of the implantable lead due at least in part to the motion of the heart during the contraction, and using the information indicative of cardiac electrical activity sensed during the contraction.

In Example 17, the subject matter of Example 16 can optionally include instructions that, when executed by the processor, cause the IMD to construct a two-dimensional template relating the information indicative of the lead movement sampled during a specified interval of time to the information indicative of cardiac electrical activity information sampled during a similar interval of time.

In Example 18 the subject matter of Examples 16 or 17 can optionally include instructions that, when executed by the processor, cause the IMD to determine a contraction metric using the two dimensional template.

In Example 19, the subject matter of Examples 16-18 can optionally include instructions that, when executed by the processor, cause the IMD to determine the contraction metric via estimating an area enclosed by a shape formed by plotting the information indicative of the movement of the implantable lead received during the contraction with respect to the information indicative of cardiac electrical activity sensed during the contraction.

In Example 20, the subject matter of Examples 16-19 can optionally include instructions that, when executed by the processor, cause the IMD to determine a contraction metric via estimating a spatial central tendency of a shape formed by plotting the information indicative of the movement of the implantable lead received during the contraction with respect to the information indicative of cardiac electrical activity sensed during the contraction.

In Example 21, the subject matter of Examples 16-20 can optionally include instructions that, when executed by the processor, cause the IMD to determine a contraction metric via estimating a spatial dispersion between a first template corresponding to a first cardiac contraction and a second template corresponding to a second cardiac contraction.

Example 22 can include subject matter, or can be combined with the subject matter of one or any combination of Examples 1-21 (such as a system, a method, a means for performing acts, or a machine-readable medium including instructions that, when performed by the machine, cause the machine to perform acts, etc.) that can include a means for obtaining information indicative of the movement of an implantable lead, the lead including a conductor electrically coupled to a receiver circuit, the receiver circuit included as a portion of an implantable medical device (IMD), and the movement due at least in part to a motion of a heart, a means for obtaining information indicative of cardiac electrical activity using a sensing circuit, and a means for constructing a template representative of a contraction of the heart, the template constructed using the information indicative of the movement of the implantable lead due at least in part to the motion of the heart during the contraction, and using the information indicative of cardiac electrical activity sensed during the contraction.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present inventors have recognized, among other things, that mechanical information indicative of cardiac, blood, or vascular motion can be detected such as by using a motion of one or more conductors electrically coupled to an ambulatory device, such as one or more conductors included as a portion of an implantable lead coupled to an IMD. Such information can be used, such as by the IMD or other device, in one or more of detecting a change to cardiovascular health, monitoring the effectiveness of a generated therapy, or guiding therapy. Information indicative of the motion of the implantable lead can be used, in addition to, or instead of sensed cardiac electrical activity.

For example, an implantable lead electrically and mechanically tethered to the IMD can provide information indicative of the motion of the lead, such as using one or more electrical measurements as described in the following examples. Such information indicative of the motion of the implantable lead can be used to adjust therapy parameters (e.g., one or more of therapy timing, a therapy delivery location, one or more therapy energy levels, etc.), or to obtain information about the effectiveness of a cardiac therapy (e.g., electrostimulation). Such monitored mechanical information can be used to obtain diagnostic information about one or more cardiac conditions or diseases. The present inventors have recognized, among other things, that such information can be obtained via measurement of variation in electrical parameters correlative to the motion of one or more therapy-conducting or activity-sensing conductors located on or within the lead assembly, without requiring a dedicated mechanical or acceleration sensor incorporated into the lead assembly.

To function, a heart initiates an electrical depolarization that can propagate through specialized accessory pathways and via myocardial cells, triggering a mechanical contraction. A relationship between cardiac electrical activity and cardiac mechanical motion can be an indicator of cardiac function, such as monitored during a cardiac contraction. For example, an electromechanical delay can be measured, such as between a triggering feature (e.g., an R wave) as indicated in sensed cardiac electrical activity, and a corresponding mechanical event (e.g., a ventricular mechanical contraction). In an example, a device, such as the IMD 105, can be configured monitor cardiac function, including electromechanical delay, such as by using information about cardiac electrical activity, or information indicative of the motion of the heart.

Figure 1:
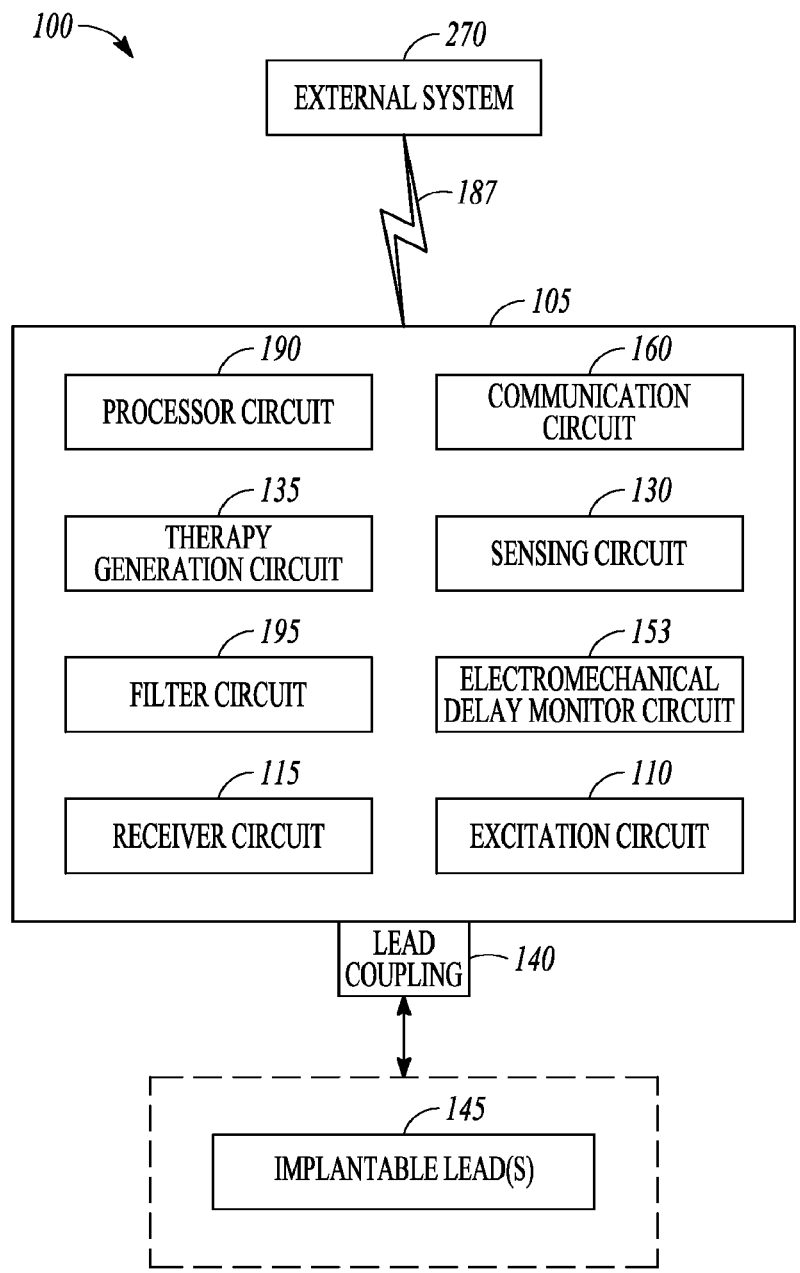
FIG. 1 illustrates generally an example of a portion of an ambulatory system for analyzing information indicative of the movement of an implantable lead.

FIG. 1 illustrates generally an example of a portion of an ambulatory system 100 that can be used for analyzing information indicative of the movement of an implantable lead. The ambulatory system 100 can include an ambulatory medical device, such as the implantable medical device (IMD) 105. The IMD 105 that can include an excitation circuit 110, a receiver circuit 115, a sensing circuit 130, a therapy generation circuit 135, an electromechanical delay monitor circuit 153, a communication circuit 160, a processor circuit 190, and a filter circuit 195. In an example, the IMD 105 can include an interconnection, such as the lead coupling 140, configured to electrically couple the IMD 105 to one or more implantable leads, such as the implantable lead 145. In an example, the IMD 105 can be communicatively coupled to an external system 270, such as by using a communicative coupling 187 (e.g., a communication or communication network, a telemetry link, an RF link, a direct wired connection, etc.).

One or more of the excitation circuit 110, the receiver circuit 115, the sensing circuit 130, the therapy generation circuit 135, the electromechanical delay monitor circuit 153, the communication circuit 160, the processor circuit 190, or the filter circuit 195 can be realized on or within a commonly shared substrate, such as on a commonly-shared integrated circuit, module, circuit board, or the like. In an example, one or more of the circuits of FIG. 1 can be included in one or more separate assemblies or separate ambulatory device, such as using one or more wired or wireless communication techniques to exchange information between such devices.

In an example, the IMD 105 can include a communication circuit 160, such as to permit wired or wireless communication using the communicative coupling 187 such as to an external system 270. The external system 270 can include such devices as a monitoring device (e.g., a local monitoring device, or a remotely located monitoring device, etc.), an ambulatory sensor, a non-ambulatory sensor, or a programmer. In an example, the ambulatory sensor or non-ambulatory sensor of the external system 270, can include the sensing circuit 130 such as can be configured to provide a signal indicative of cardiac electrical activity (e.g., at least a portion of a surface ecg).

The system 100 or the external system 270 can include processing capability, such as included within the IMD 105, the monitoring device, the ambulatory sensor, or the non-ambulatory sensor. Thus, various techniques can be implemented at one or more of such locations, such as on-board the IMD 105 or at one or more externally, either locally or at a more remote location. In an example, the IMD 105 can include processing capability, such as the processor circuit 190. For example, the various techniques can be implemented such as using an application-specific integrated circuit (ASIC) configured to perform one or more functions, or a general-purpose circuit programmed to perform such functions. Such a general-purpose circuit can include a microprocessor, a microcontroller, or a programmable logic circuit, or a portion of one or more of these. In an example, one or more portions of various techniques can be distributed between such locations. In an example, the IMD 105, or a similar device in the external system 270, can include a processor-readable medium such as a memory circuit (e.g., an EEPROM, an SRAM, or one or more other memory technology devices). The processor circuit 190 can be configured to perform one or more instructions stored on the processor-readable medium.

In an example, the IMD 105 can include an excitation circuit, such as the excitation circuit 110 that can be coupled to at least one of the receiver circuit 115 or the implantable lead 145. The excitation circuit 110 can be configured to provide a time varying signal including a first range of frequencies such as including a non-tissue stimulating, non-therapeutic electrical excitation signal, such as for coupling to the implantable lead 145. In an example, the excitation signal can include a time-varying voltage or current including one or more frequencies within a specified frequency range (e.g., a range from about 10 KHz to about 5 MHz, from about 5 MHz to about 30 MHz, from about 30 MHz to about 150 MHz, or including one or more other ranges of frequencies). In an example, the excitation signal can include a pulsed electrical signal, such as including one or more current or voltage pulses including a specified or desired amplitude, duration, pulse repetition rate, duty cycle, or morphology, among other parameters.

In an example, the excitation circuit 110 can be coupled to one or more implantable leads, such as the implantable lead 145 via the lead coupling 140. The lead coupling 140 can include a header or other connector included as a portion, part, or component of the IMD 105. In an example, an impedance measurement can be made at least in part using the excitation circuit 110, such as to obtain the information indicative of lead motion. The impedance measurement can include injecting a current between a first terminal such as at least a portion of the lead coupling 140 and one or more other conductive elements, such as the housing of the IMD 105, or a second terminal, and measuring the voltage developed across the respective conductive elements. In an example, a synchronous current injection and voltage measurement can be used, such as discussed in relation to the physiologic impedance measurement techniques of the commonly assigned U.S. patent application Ser. No. 12/350,728, entitled "IMPEDANCE MEASUREMENT AND DEMODULATION USING IMPLANTABLE DEVICE," filed on Jan. 8, 2009, published as U.S. 2009/0177110, which is herein incorporated by reference in its entirety, including its description of injecting one or more non-tissue-stimulating bi-phasic current pulses and synchronously measuring the voltage induced by the one or more bi-phasic current pulses.

In an example, the implantable lead 145 can be coupled to circuitry within the IMD 105 such as via the lead coupling 140 (e.g., a header or other connector block included as a portion of the IMD 105). For example, the implantable lead 145 can include one or more conductors (e.g., a cardiac therapy delivery conductor, a cardiac electrical activity sensing conductor, etc.) that can provide electrical coupling between one or more electrodes located at or near tissue (e.g., cardiac tissue, neural tissue, etc.) and the IMD 105. In an example, the implantable lead 145 can be located at a site within or on the body (e.g., including one or more surface, subcutaneous, or intravascularly-located electrodes or conductors).

In an example, the receiver circuit 115 can be electrically or communicatively coupled to an implantable lead 145 such as through the lead coupling 140. For example, one or more separate conductors in the implantable lead 145 can be attached to one or more terminal blocks such as included in a lead coupling 140 attached to a housing of the IMD 105. For example, the lead coupling 140 can provide electrical contact between one or more conductors of the implantable lead 145 and circuitry within the IMD 105 (e.g., excitation circuit 110, the receiver circuit 115, the therapy generation circuit 135, etc.). In an example, the receiver circuit 115 can be configured to receive a response signal, such as including a signal indicative of the motion of the implantable lead, hereinafter referred to as a lead motion indicating (LMI) signal. For example, a response signal can be obtained in response to an interaction between an excitation signal, such as provided by the excitation circuit 110, and the electrical characteristics of the implantable lead 145 (e.g., one or more motion-dependent passive electrical characteristics of the lead) such as during a movement of the implantable lead 145. For example, such electrical characteristics of the lead can vary as portions of the lead are compressed or flexed, such as altering the spacing between portions of one or more conductors included in the lead assembly. In an example, the receiver circuit 115 can be configured to receive or process one or more response signals obtained from one or more implantable leads 145 concurrently with or subsequently to the excitation circuit 110 providing the excitation signal to the one or more implantable leads. For example, the receiver circuit 115 can be configured to receive magnitude information or phase information corresponding to one or more frequencies included in a range of frequencies provided in the excitation signal. In an example, the magnitude information or the phase information can include time-varying information such that can include information indicative of the movement of the implantable lead 145.

For example, the receiver circuit 115 can be configured to obtain information about the movement of a first implantable lead located (e.g., a first LMI signal), such as located within or near a first location of the heart using a first response signal obtained from the first implantable lead. Additionally, the receiver circuit 115 can be configured to obtain information about the movement of a second implantable lead (e.g., a second LMI signal), such as located within or near a second location of the heart, using a second response signal obtained from the second implantable lead. For example, the information about the movement of an implantable lead can be determined or extracted from the LMI signal (e.g., using information about an amplitude, a frequency, a phase, a noise floor, a signal-to-noise ratio, a duration between peaks or other features, a waveform morphology or shape, or one or more other characteristics of the LMI signal).

In an example, the receiver circuit 115 can be configured to process the response signal (e.g., using a filter), such as to provide a time-varying signal indicative of the motion of the implantable lead (e.g., the LMI signal) for analysis. For example, the response signal can include a first component (e.g., a carrier signal), such as including information about the excitation signal, and a second component (e.g., a signal indicative of lead motion that can modulate the carrier), such as the LMI signal. In an example, the LMI signal can include time-varying information indicative of the motion of the implantable lead. In an example, the receiver circuit 115 can be configured to transfer at least a portion of the LMI signal to a circuit configured for signal processing (e.g., processor circuit 190, etc.) to be analyzed. For example, the processor circuit 190 can analyze at least a portion of the LMI signal such as to obtain information indicative of the motion of the implantable lead such that can contain information about a cardiac mechanical contraction (e.g., a mechanical contraction waveform).

In an example, the receiver circuit 115 can be configured to determine amplitude information of one or more LMI signals. For example, the amplitude information can be determined such as by using one or more of a central tendency (e.g., an average, a median, a mean, etc.), a peak-to-peak determination, a peak determination, a root-mean-square determination, a relative indication of information about a portion of the LMI signal (e.g., a percentage of an absolute or local maximum or minimum), or an absolute value of at least a portion of the LMI signal. In an example, the receiver circuit 115 can be configured to analyze at least a portion of the LMI signal, such as to compare amplitude information obtained from the LMI signal to a criterion (e.g., a threshold) or to amplitude information corresponding to a second LMI signal. The receiver circuit 115 can use such an analysis to determine whether the LMI signal can be sent for further analysis, such as by the processor circuit 190.

In an example, the IMD 105 can include a filter circuit 195 such as can be communicatively coupled to one or more of the receiver circuit 115 or the processor circuit 190. In an example, the filter circuit 195 can be configured to provide an LMI signal (e.g., a mechanical contraction waveform) from the response signal. For example, the filter circuit 195 can provide the LMI signal such as by using band-pass filter over a specified frequency range (e.g., from about 0.5 Hz to about 10 Hz) such that the processor circuit 190 can provide information indicative of the motion of the implantable lead. For example, a band-pass filter such as configured to pass frequencies between about 0.5 Hz and about 2 Hz can be used to provide a mechanical contraction waveform (e.g., a signal, a time-series, or other information) indicative of the mechanical contraction of the heart. The mechanical contraction waveform can be conditioned such that the waveform has a zero average over long intervals or can approach zero during an interval of no motion. Although band-pass filters are generally described, any combination of analog or digital filters can be used, including a one or more high pass filters, low pass filters, notch filters, passive filters (e.g., having "T" sections, "π" sections, "L" sections, etc.), active filters (e.g., Bessel filter, Chebyshev filter, Butterworth filter, etc.), IIR filters, FIR filters, or the like.

In an example, the IMD 105, or a device in the external network 270 via the communication link 187, can include a processor circuit 190, configured to be communicatively coupled to one or more of the excitation circuit 110, the receiver circuit 115, the sensing circuit 130, the therapy generation circuit 135, or the filter circuit 195. In an example, the processor circuit 190 can be configured such as to determine information about cardiac function, such as including information about electromechanical delay of the heart over one or more cardiac contraction cycles. For example, the processor circuit 190, or the IMD 105, can include an electromechanical delay monitor circuit 153.

In an example, the processor circuit 190 can be configured to receive information indicative of the motion of an implantable lead, such as an LMI signal, from one or more of the receiver circuit 115 or the filter circuit 195. In an example, the processor circuit 190 can be configured to receive a signal indicative of cardiac electrical activity, such as from the sensing circuit 130 or a sensor included in the external system 270 (e.g., an ambulatory sensor or a non-ambulatory sensor). The processor circuit 190 can be configured to determine whether a cardiac mechanical contraction occurred during a specified interval, such as included in at least a portion of the LMI signal, such as a mechanical cardiac waveform. In an example, the processor circuit 190 can be configured to determine a relationship between an indication of cardiac electrical activity and an indication of cardiac mechanical motion, such as determined using at least a portion of an LMI signal and a portion of the signal indicative of cardiac electrical activity. For example, the processor circuit 190 can be configured to determine an electromechanical delay over one or more cardiac contraction cycles, such as by determining a relationship between the signal indicative of cardiac electrical activity and the LMI signal.

Movement of the implantable lead 145 can include a physical displacement of one or more portions of the implantable lead 145, such as with respect to an equilibrium position. In an illustrative example, the implantable lead 145 can undergo a physical displacement, such as from a mechanical coupling to, or physical contact with, moving tissue. In an example, the information indicative of movement of the implantable lead 145 can include a time varying signal (e.g., the LMI signal), where the LMI signal corresponds to a movement of the heart (e.g., a cardiac contraction cycle, an impact of a heart valve to the implantable lead 145, a frictional contact of cardiac tissue to the implantable lead 145, or mechanical contact of the lead to vibrating tissue, etc.).

In an example, the processor circuit 190 can be configured to obtain the mechanical contraction waveform at least in part using one or more filters, such as using the filter circuit 195. In an example, the processor circuit 190 can be configured such as to obtain a mechanical contraction waveform corresponding to the mechanical motion of at least a portion of a heart (e.g., one or more of the right atrium, left atrium, right ventricle, or left ventricle). For example, the response signal, such as obtained by the receiver circuit 115, can be filtered using a band-pass filter configured to pass frequencies within a specified frequency range, such as between about 0.05 Hz and about 10 Hz, such as discussed below with FIG. 8. In an example, the filtered signal (e.g., the LMI signal) can include a waveform indicative of one or more cardiac mechanical contractions. In an example, the processor circuit 190 can be configured to analyze the mechanical contraction waveform continuously. In an example, the processor circuit 190 can be configured to analyze a specified duration of lead motion information including one or more mechanical contractions, such as a specified duration of contraction information obtained at a specified time (e.g., once a minute, hourly, daily, weekly, etc.), or obtained following a specified event (e.g., a user initiated event, an occurrence of a physiological event, or in response to one or more other criteria).

In an example, the processor circuit 190 can obtain a composite mechanical contraction waveform, such as by using a mixer circuit. Such composite mechanical contraction waveforms can include information about a motion originating in or detected nearby an atrial region, a motion originating in or detected nearby a ventricular region, other motion of the implantable lead independent of the motion of the heart, or a vibration such as due to a valve impact against a region of the lead. For example, the mixer circuit can combine one or more mechanical contraction waveforms additively, such as to provide a composite mechanical contraction waveform having information about atrial and ventricular contractions. In an example, the mixer circuit can be configured to combine at least a portion of two or more mechanical contraction waveforms such as to provide a mechanical contraction waveform primarily associated with ventricular motion or primarily associated with atrial motion.

Figure 5C:
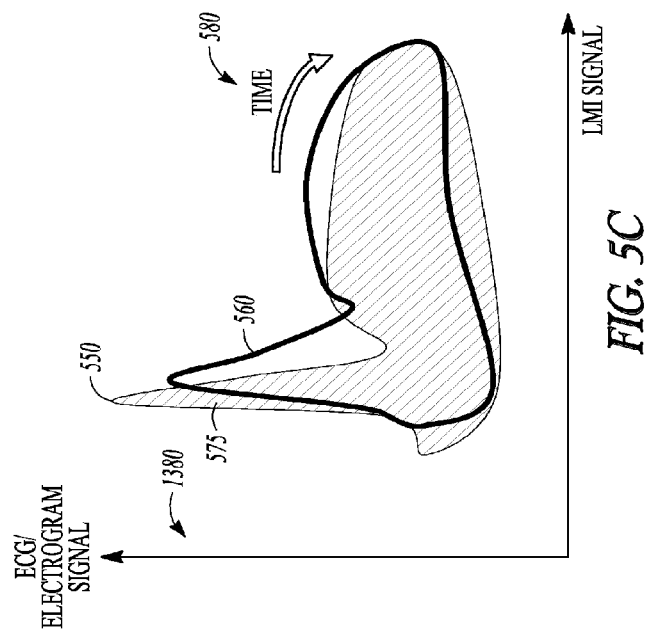
FIGS. 5A-5C illustrate generally an example of a relationship between a signal indicative of cardiac electrical activity and a signal indicative of the movement of the implantable lead.
Figure 5A:
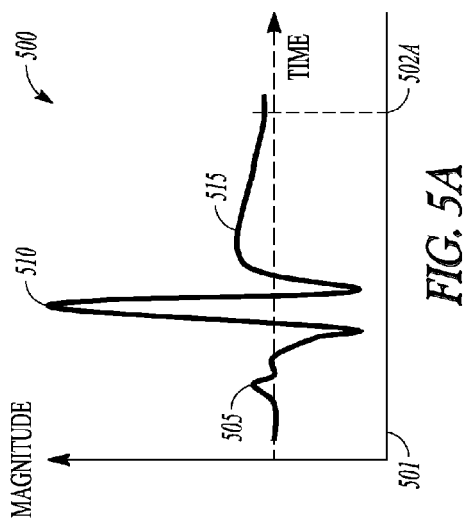
Figure 5B:
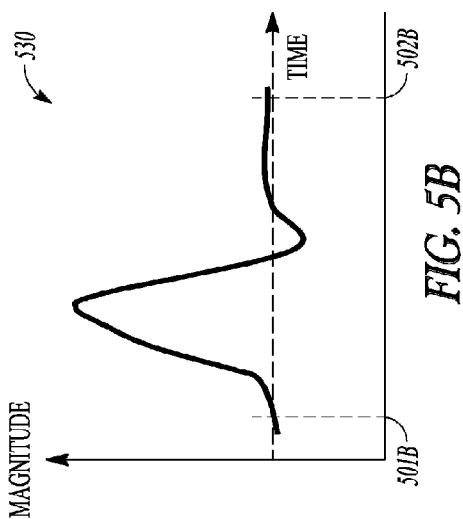

In an example, the processor circuit 190 can be configured to obtain electrical activity information such as using a signal indicative of cardiac electrical activity over one or more cardiac contraction cycles (e.g., from the sensing circuit 130 or from an ambulatory or non-ambulatory sensor such as included in the external network 270). For example, the electrical activity information can include an electrical signal as can be represented by an electrogram over at least a portion of one or more cardiac contraction cycles (e.g., a cardiac electrical activity waveform such as shown in FIG. 5A). In an example, the processor circuit 190 can be configured to obtain mechanical motion information about the heart, such as from an LMI signal over the one or more cardiac contraction cycles (e.g., from the receiver circuit 115, or the filter circuit 195). For example, the mechanical motion information can include at least a portion of one or more mechanical contraction waveforms as shown in FIG. 5B.

In an example, the processor circuit 190 can be configured to determine information about the relationship between cardiac electrical activity and cardiac mechanical motion using the obtained electrical activity information and the mechanical motion information (e.g., a template representative of the electromechanical operation of the heart such as by using the electrical activity information and the mechanical motion information). For example, the processor circuit 190 can be configured to determine a two-dimensional template such as relating cardiac electrical activity vs. cardiac mechanical activity as can be representative of a contraction of the heart, as shown in FIG. 5C. The template can include a path corresponding to the relationship between the electrical activity information and the mechanical motion information over time. For example, the path can include a continuous path (e.g., substantially similar electromechanical information at the start and end of a cardiac contraction cycle) or a discontinuous path (e.g., differing electromechanical information at the start of the cardiac contraction cycle and the end of the cardiac contraction cycle).

In an example, the processor circuit 190 can be configured to construct a template representative of a contraction of the heart using information about multiple contractions. For example, the template can be constructed such as by using a central tendency (e.g., an average, a mean, a median) of the information indicative of cardiac electrical activity over two or more cardiac contraction cycles or a central tendency of the information indicative of the movement of the implantable lead over two or more cardiac contraction cycles. In an example, the processor circuit 190 can be configured to construct the template using mechanical motion information obtained from one or more implantable leads, or electrical activity information from one or more sensing circuits or locations (e.g., one or more electrode locations, such as included on an implantable lead or with a surface ecg). In an example, the template can be constructed electrical activity information or mechanical motion information obtained continuously. In an example, the template can be constructed using electrical activity information or mechanical motion information obtained such as during a specified duration at a specified interval (e.g., about 20 ms) over one or more cardiac contraction cycles. In an example, the processor circuit 190 can be configured to condition (e.g., scale or normalize, or otherwise process at least one of the electrical activity information or the mechanical motion information. For example, the template can include a shape formed by plotting the information indicative of the lead motion obtained during the contraction with respect to the information indicative of the electrical activity sensed during the contraction.

In an example, the processor circuit 190 can be configured to determine a contraction metric such as by using the template, such as including the shape formed by plotting information included in an LMI signal (e.g., a mechanical contraction waveform) and the information indicative of cardiac electrical activity (e.g., an ecg waveform). For example, the contraction metric can include an area, a central tendency (e.g., a coordinate-wise mean such as a centroid), a morphological feature of at least a portion of the shape, or a slope (e.g., a gradient, a curvature, etc.) of at least a portion of the shape. In an example, the processor circuit 190 can be configured to compare a first template associated with a normal sinus rhythm and a second template associated with a different mechanical contraction waveform (or a composite of other waveforms). The processor circuit 190 can be configured to compare two or more templates such as by using a spatial dispersion (e.g., an eigenvalue of a covariance matrix), a difference between similar portions of the template, an indication of rotation between the two templates, or the like.

In an example, the processor circuit 190 can be configured to determine an indication of a physiological condition, such as by using the contraction metric. In an example, the processor circuit 190 can be configured such as to determine an indication of cardiac function (e.g., a change in cardiac electromechanical timing relationship such as electromechanical delay) such as can be used to diagnose a physiological condition (e.g., ischemia, congestive heart failure (HF), an arrhythmia, etc.) using one or more contraction metrics. For example, a disease that can affect cellular function (e.g., cause an impaired calcium cycling within the cells) can be indicated such as by an increased electromechanical delay of the heart (e.g., an increase of 100 ms or more).

For example, one or more contraction metrics (e.g., a centroid, morphological feature of at least a portion of the template, an area, etc.) can be used to determine an indication of an abnormal electromechanical delay. For example, an increased electromechanical delay can cause the template morphology to differ from the template indicative of a normal sinus rhythm. For example, an increase in electromechanical delay within the heart can affect cardiac electrical activity (e.g., a wide QRS structure) or the cardiac mechanical contraction (e.g., a decrease in the magnitude of the mechanical contraction waveform) such as resulting in a change to the constructed template. The resulting template constructed using the electrical activity information and the mechanical motion information can result in an indication of abnormal cardiac electromechanical activity (e.g., as compared to the template indicative of normal cardiac activity). In an example, the template indicative of normal cardiac activity can be determined using information from a single subject, or information aggregated from a specified population.

In an example, the processor circuit 190 can be configured to determine a trend associated with cardiac electromechanical function using one or more contraction metrics. Data trending can be performed using various forms of regression analysis, such as a linear regression, a non-linear regression, a least-squares technique, a Bayesian technique, a quintile regression, or a nonparametric regression, or using one or more other techniques.

In an example, the processor circuit 190 can be configured to compare one or more contraction metrics over a specified duration such as including two or more successive or adjacent cardiac contraction cycles. For example, the processor circuit 190 can determine an indication of an altered electromechanical function, such as electrical alternans (e.g., a repolarization alternans such as a ST alternans, a conduction and refractoriness alternans such as a QRS alternans, or other alternans) or mechanical alternans (e.g., pulsus alternans). In an example, the processor circuit 190 can determine a difference between two or more consecutive cardiac contraction cycles such as by using one or more contraction metrics. Examples of the difference between two or more consecutive cardiac contraction cycles can include a morphological change to at least a portion of the template shape, a change to a spatial central tendency of the template shape, or using a spatial dispersion determination (e.g., an eigenvalue of a covariance matrix corresponding to two-dimensional information representative of the template).

In an example, pulsus alternans can be indicated such as by alternating strong and weak beat. Pulsus alternans can indicate left ventricular systolic impairment. The processor circuit 190 can be configured to determine the indication of pulsus alternans such as by determining a pattern (e.g., an alternating strong contraction and weak contraction), such as included in the contraction metrics over a series of consecutive cardiac contraction cycles.

In an example, the system 100 can include the sensing circuit 130, such as to obtain a signal indicative of cardiac electrical activity. For example, the obtained signal can be used to provide a graphical representation of the cardiac electrical activity, such as an intracardiac electrogram or a surface ecg. In an example, the IMD 105 can be configured to detect a cardiac condition (e.g. an arrhythmia) or therapy effectiveness (e.g., cardiac capture following a electrostimulation pulse), such as using signal information (e.g., magnitude or interval information) detected using the sensing circuit 130, such as magnitude or interval information from the signal representative of cardiac electrical activity. For example, the processor circuit 190 can be configured to use electrogram timing information, such as a time interval obtained between successive atrial contractions, ventricular contractions, or between an atrial contraction and a ventricular contraction.

In an example, the timing information can be compared to a criterion, such as to detect or classify an indication of an arrhythmia when the criterion has been met (e.g., exceeding a threshold, lying within or outside of a specified range, etc.). In an example, the timing information can include a timing reference corresponding to a magnitude meeting a specified criterion. For example, the timing reference can include a duration (e.g., such as a duration during which a magnitude exceeds a value or remains within a specified range of values), or a fiducial (e.g., such as a time associated with a magnitude crossing a specified threshold). For example, the criterion (e.g., the specified range of values, or the specified threshold) can vary automatically, such as by using automatic gain control. In an example, the criterion can vary based on one or more physiological conditions, such as can be detected using the signal information (e.g., a magnitude or timing information of a signal indicative of cardiac electrical activity).

In an example, the IMD 105 can be configured to generate an electrostimulation, such as using one or more of a pacing or a cardiac resynchronization therapy (CRT) circuit (e.g., the therapy generation circuit 135). Such a therapy generation circuit 135 can be configured to generate bradycardia pacing or a resynchronization electrostimulation therapy for delivery to cardiac tissue, or one or more other therapies. In an example, the therapy generation circuit 135 can include a neural stimulator device, such as to provide electrical, mechanical, optical, acoustic or chemical stimulation to one or more neural targets.

In an example, the therapy generation circuit 135 can include one or more of: a pacing circuit, an anti-tachyarrhythmia therapy circuit, a cardiac resynchronization therapy circuit, a cardiac contractility modulation (CCM) circuit, or one or more other therapy generation circuits. For example, the anti-tachyarrhythmia therapy circuit can include a defibrillation circuit, or an anti-tachyarrhythmia pacing (ATP) circuit, or the like. In an example, the therapy generation circuit 135 can be configured to determine a therapy, or therapy protocol, such as to guide an arrhythmia therapy.

In an example, the therapy generation circuit 135 can be configured to withhold generation of a therapy such as when an arrhythmia condition is not present. In an example, the therapy generation circuit 135 can be configured to withhold, or delay, generation of an arrhythmia therapy, such as when a rhythm, such as a detected arrhythmia, has been determined to be supraventricular in origin.

In an example, the therapy generation circuit 135, or the processor circuit 190, can be configured to automatically adjust one or more of an electrostimulation pulse width, an electrostimulation pulse amplitude, or a timing of delivery of electrostimulation therapy. For example, the processor circuit 190 can be configured to monitor the mechanical contraction waveform after the therapy generation circuit 135 generating a therapy to the heart (e.g., pacing energy). In response to information obtained while monitoring the therapy, the processor circuit 190 can determine information corresponding to the effectiveness of the delivered therapy (e.g., captured the myocardium, achieved fusion or another specified timing relationship between paced ventricular activation relative to an intrinsic atrial beat, or improved cardiac synchrony via CRT).

Figure 2:
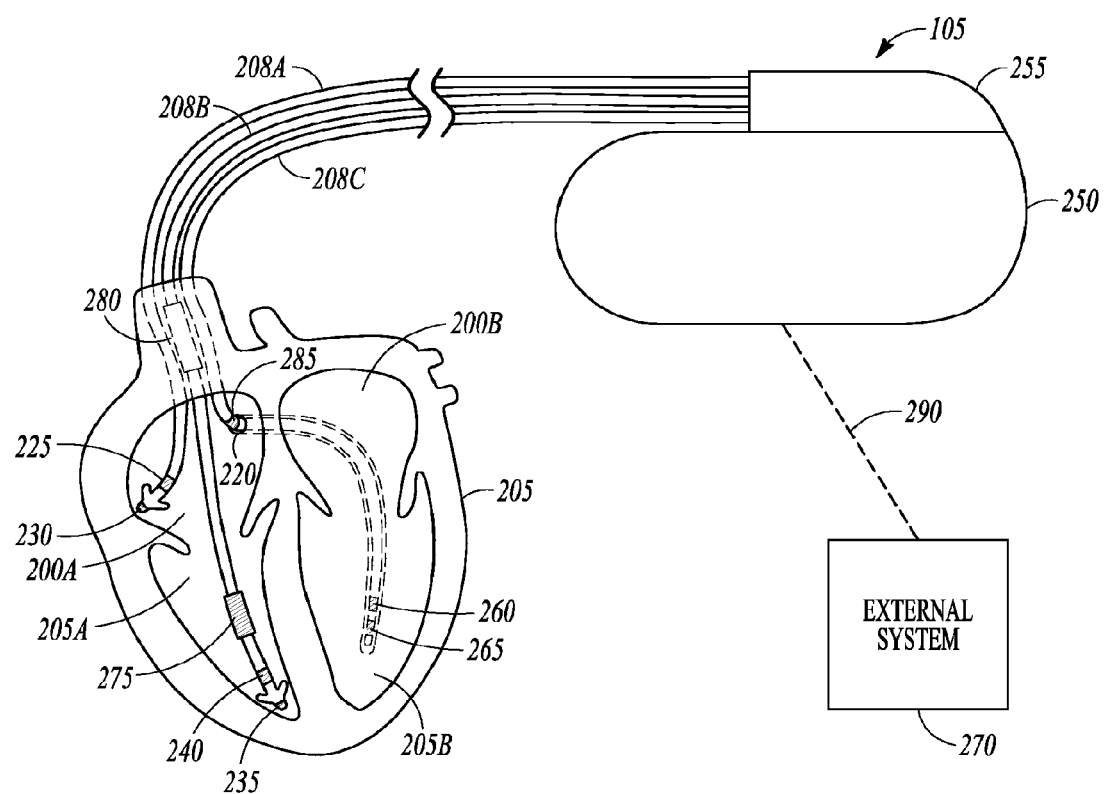
FIG. 2 illustrates generally a portion of a system that can include an implantable medical device.

FIG. 2 illustrates generally a portion of a system that can include an IMD 105. Examples of the IMD 105 can include cardiac function management (CFM) devices such as including one or more of implantable pacemakers, implantable cardioverter-defibrillators (ICDs), cardiac resynchronization therapy devices (CRTs), or one or more other devices. The system can include an IMD programmer or other external device 270, such as a local monitoring device, capable of communicating wirelessly, via communicative coupling 290, with the IMD 105, using a communication or computer network, radio frequency (RF) signals, or other telemetry capabilities. In an example, a remote monitoring device can be communicatively coupled, such as via a communication or computer network, to a remote monitoring device, such as at a remote location away from the local monitoring device (e.g., a central server, a caregiver workstation, etc.).

The IMD 105 can be coupled via one or more leads 208A-C to the heart 205. Cardiac leads 208A-C (e.g., the implantable lead 145) can include a proximal end coupled to the IMD 105 and a distal end, capable of being electrically coupled by one or more electrodes to one or more portions of the heart 205. The electrodes can deliver cardioversion, defibrillation, pacing, or resynchronization therapy, or combinations thereof, such as from the therapy generation circuit 135, to one or more chamber of the heart 205. The electrodes can be electrically coupled to sense amplifiers configured to receive electrical signals indicative of cardiac activity, such as the sensing circuit 130.

The heart 205 includes a right atrium 200A, a left atrium 200B, a right ventricle 205A, a left ventricle 205B, and a coronary sinus 220 extending from right atrium 200A. The atrial lead 208A can include electrodes (e.g., electrical contacts, such as a ring electrode 225, and a tip electrode 230, etc.) capable of being disposed in the atrium 100A of the heart 205, such as for sensing signals, delivering pacing therapy, or both, to the atrium 200A.

The ventricular lead 208B can include one or more electrodes, such as the tip electrode 235 or the ring electrode 240, such as for sensing signals, delivering pacing therapy, or both. The lead 208B optionally can include additional electrodes, such as for delivering atrial cardioversion, atrial defibrillation, ventricular cardioversion, ventricular defibrillation, or combinations thereof to the heart 205. Such electrodes can have larger surface areas than do pacing electrodes, such as to handle larger energies involved in defibrillation. In an example, the lead 208B can deliver resynchronization therapy to the heart 205.

The IMD 105 can include a third cardiac lead 208C capable of being attached to the IMD 105 through the header 255. The third cardiac lead 208C can include one or more electrodes such as electrodes 260 and 265, such as placed in a coronary vein nearby the left ventricle (LV) 205B. The third cardiac lead 208C can include a ring electrode 285, such as positioned near the coronary sinus (CS) 220.

The lead 208B can include one or more of a first defibrillation coil electrode 275, such as located proximal to the tip and ring electrodes 235, 240, such as for placement in a right ventricle (RV), or a second defibrillation coil electrode 280, such as located proximal to the first defibrillation coil 275, the tip electrode 235, and the ring electrode 240, such as for placement in or near the superior vena cava (SVC). In an example, a cardioversion or a shock therapy can be delivered from the first coil (e.g., the RV coil 275) to the second coil (e.g., the SVC coil 280). In an example, the SVC coil 280 can be electrically tied to an electrode formed on a hermetically-sealed IMD housing 250 ("can"), such as to provide an adjustable defibrillation "vector" or "pathway" for energy to pass between the RV coil 275 and the housing 250 via the myocardium. In an example, the therapy can be delivered from the RV coil 275, such as only to the electrode formed on the IMD can 250. The present methods and systems can be adjustably configured to provide one or more pacing or defibrillation therapies across specified electrode configurations, such as using information about electrical or mechanical cardiac activity as described in the examples above and below.

Figure 3:
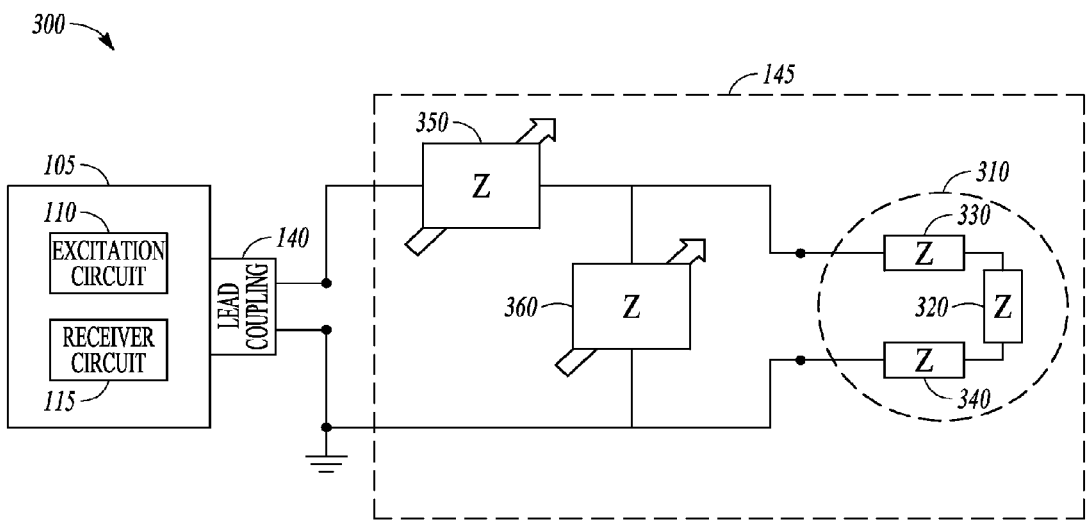
FIG. 3 illustrates generally a portion of a system that can include detecting information indicative of the movement of the implantable lead.

FIG. 3 illustrates generally a portion of a system 300 that can include detecting information indicative of the movement of one or more implantable leads, such as the implantable lead 145. In an example, the system 300 can include an IMD 105, and the implantable lead 145, such as configured to provide a therapy (e.g., an arrhythmia therapy) to a heart 205, to sense a physiological signal associated with a subject (e.g., an electrogram), or both. In an example, the IMD 105 can include the excitation circuit 110 and the receiver circuit 115, and the lead coupling 140 as described above. In an example, the implantable lead 145 can be configured to be implanted within a subject such that a distal end of the lead body 310 can be located within or near the heart 205 (e.g., at a tissue interface location), and a proximal end can be configured to be electrically coupled to the IMD 105 (e.g., at the lead coupling 140), such as to provide a therapy, to sense a physiological signal, or both. In an example, the excitation circuit 110 can be configured to provide an excitation signal to the implantable lead 145. Such an excitation signal can interact with the electrical characteristics of the implantable lead such as to provide a response signal, as can be obtained by the receiver circuit 115.

In an example, the implantable lead 145 can include one or more conductors (e.g., filers), such as one or more filers that spiral or otherwise traverse the length of the lead, such as from a connector at the proximal end of the lead to one or more electrodes along the lead or near the distal end. In an example, a lead body can be represented as a combination of resistive, capacitive, and inductive elements. In an example, the electrical characteristics of the implantable lead can be represented, such as using lead body impedance (e.g., lead impedance 350-360) and the distal end of the lead can be modeled, such as using one or more of an electrode impedance 330-340, a cardiac tissue interface impedance 320, or the like. In an example, the impedance 330-360 can represent the electrical characteristics of various lead portions (e.g., passive electrical characteristics such as the resistance of a filer, an inductance of a loop formed by one or more filers, a capacitance between one or more filers, etc.) over a specified frequency range. In an example, the tissue interface impedance can include electrode impedance, such as a characteristic impedance of an electrode, and an impedance 320 at the tissue interface, such as an impedance corresponding to a connection of the implantable lead to the cardiac tissue.

In an example, the frequency dependent components of the impedances 320-360 can vary over a specified frequency range (e.g., from about 10 KHz to about 30 MHz, from about 30 MHz to about 150 MHz, etc.), corresponding to one or more of capacitive or inductive coupling between two or more portions of the implantable lead 145. In an example, an implantable lead can include an active element, such as an accelerometer, or piezoelectric elements, that can be used to obtain information about the motion of the implantable lead 145 separately from, or additionally to the passive electric characteristics.

Figure 6:
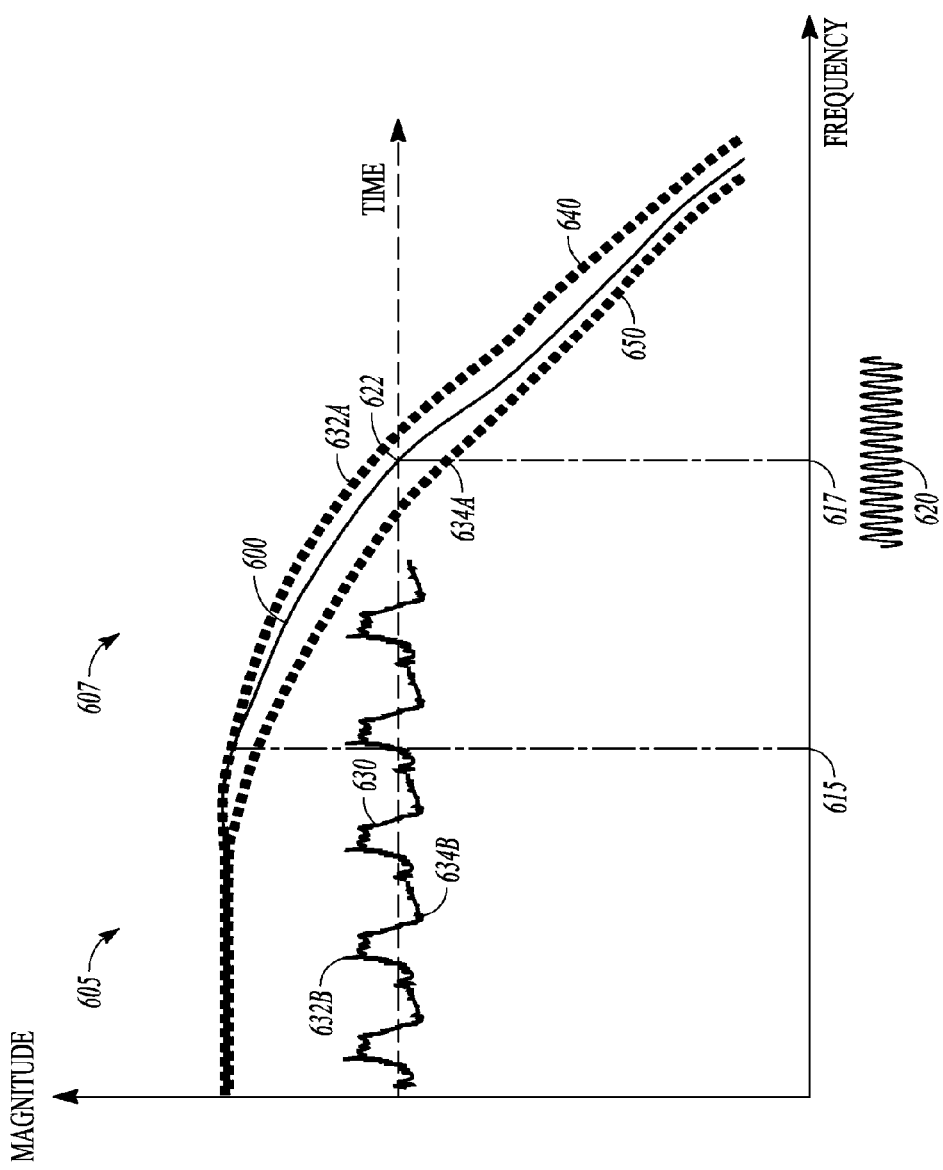
FIG. 6 illustrates generally an illustrative example of a relationship between a magnitude of a response signal vs. frequency.

In an example, the electrical characteristics of the implantable lead can vary as a function of frequency, such as shown in FIG. 6, over a specified frequency range (e.g., from about 10 KHz to about 100 KHz, from about 10 KHz to about 30 MHz, from about 10 MHz to about 150 MHz, etc.), such as a result of the capacitive or inductive interaction between a conductive portion of the lead and another conductor either located within the lead or elsewhere. In an example, the implantable lead 145 can be physically connected to the heart 205, or physically located near or within the heart 205, such that movement of the heart (e.g., a cardiac contraction cycle) can result in movement of the lead body. Such movement of the lead body can cause a corresponding change to the electrical characteristics (e.g., lead capacitance, lead inductance, etc.).

For example, the lead impedances 350-360 can vary as a function of time corresponding to the movement of the implantable lead, such as during a cardiac cycle. Lead motion can include movement, or physical manipulation, of the implantable lead due to motion, such as caused by a cardiac contraction cycle (e.g., bending, stretching, twisting, impact, torsion, compression, etc.). In an example, the motion of the implantable lead 145 can include physical disturbance to the lead due to impact (e.g., a heart valve impact), frictional movement (e.g., frictional contact to cardiac tissue, or other tissue), radial compression (e.g., such as due to variation in blood pressure), or the like. In an example, lead motion can include, physical translation, or rotation of the lead body relative to a point fixed in space (e.g., a point on the body, inertial frame, etc.), such as might be measurable with a lead based accelerometer.

Figure 4:
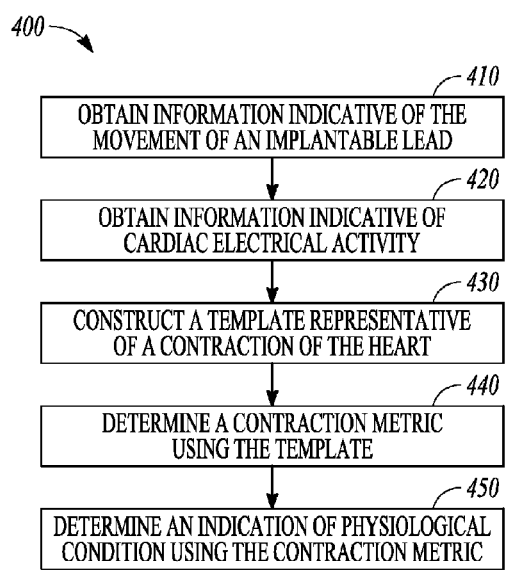
FIG. 4 illustrates generally an example of a technique that can include analyzing information indicative of the movement of the implantable lead.

FIG. 4 illustrates generally an example of a technique for analyzing information indicative of the movement of the implantable lead. At 410, an LMI signal can be obtained, such as from a response signal obtained from the implantable lead 145, as described above. For example, the LMI signal can be processed, such as using a filter, to determine a mechanical contraction waveform (e.g., such as including mechanical contraction information) indicative of the motion of the implantable lead over one or more cardiac contraction cycles.

At 420, information indicative of cardiac electrical activity can be obtained such as by the sensing circuit 130, as described above. In an example, the electrical activity information can be obtained substantially during the same duration as the LMI signal.

At 430, mechanical contraction information and electrical activity information can be used such as to construct a template representative of a contraction of the heart. For example, the processor circuit 190 can be configured such as to construct a shape, such as over one or more cardiac contraction cycles, using the mechanical contraction information and the electrical activity information. A shape can be constructed such as by plotting the electrical activity information vs. the mechanical contraction information over a duration including one or more cardiac contraction cycles. In an example, the shape can be constructed using a central tendency (e.g., median, average, etc.) of the mechanical contraction information or a central tendency of the electrical activity information over one or more cardiac contraction cycles.

At 440, a contraction metric can be calculated using the template. For example, calculating the contraction metric, such as by the processor 190, can include estimating an area of the shape included in the template, calculating a central tendency (e.g., a centroid), or determining information about a morphological feature of at least a portion of the shape. In an example, the contraction metric can be calculated such as by determining a spatial dispersion (e.g., an eigenvalue of a covariance matrix), or a difference (e.g., a difference between areas, rotation information, etc.) between a first template corresponding to a first cardiac contraction and a second template corresponding to a second cardiac contraction. For example, the first template can correspond to a representation of a sinus cardiac contraction cycle such as can be determined during a time of known cardiac contraction activity, or can be calculated such as from information corresponding to a substantially similar population.

At 450, one or more contraction metrics can be used to determine an indication of a physiological condition of the subject, such as by the processor 190. A first contraction metric (e.g., an area, a centroid, etc.) corresponding to a template associated with a sinus contraction cycle over a first duration can be compared to a second contraction metric corresponding to a template constructed from a second duration (e.g., a current duration) such as to indicate a change to a physiological condition of the subject. For example, a difference, such as can be indicated by meeting a criterion (e.g., exceeding a threshold) between the first and second contraction metrics can correspond to a change in physiological condition. In an example, the criterion can vary as a function of one or more of the LMI signal, the signal indicative of cardiac electrical activity, or other physiological signals such as can be obtained using the sensing circuit 130.

FIGS. 5A-5C illustrate generally an example of a relationship between a signal indicative of the movement of the implantable lead and a signal indicative of cardiac electrical activity. FIG. 5A illustrates generally a representation of a signal 500 indicative of cardiac electrical activity over a cardiac cycle. For example, the signal 500 includes electrical activity information (e.g., a P wave 505, an R wave 510, and a T wave 515, etc.) over a cardiac cycle such as between times 501A, 502A. FIG. 5B illustrates generally a representation of a signal 530 such as an LMI signal over a duration substantially similar to the duration of FIG. A (e.g., between times 501B, 502B).

FIG. 5C illustrates generally an example of a relationship between two templates such as can be constructed using the mechanical motion information, such as from the LMI signal 530 of FIG. 5B, and the electrical activity information such as from the signal 500 of FIG. 5A. In an example, the shape 550 can correspond to the electromechanical function of a heart such over a duration associated with a normal cardiac contraction cycle. The shape 560 can correspond to information corresponding to a second duration associated with one or more cardiac contraction cycles (e.g., at a current duration). In an example, an indication of the physiological condition of the subject can be determined such as by using a comparison of the shapes such as by comparing a metric (e.g., an area, a centroid, morphology over at least a portion of the cardiac contraction cycle, an eigenvalue, an indication of rotation, etc.) as described above.

In an example, at least a portion of the signal indicative of cardiac electrical activity 500 and at least a portion of a cardiac contraction waveform 530 can be used to construct a two dimensional shape such as the shapes 550, 560. For example, a magnitude of a portion of an electrogram signal can be plotted against the magnitude of a portion of an LMI signal such that time 580 corresponds to a clockwise path around the shape. In an example, the signals 500, 530 can be conditioned (e.g., scaled) such that the shape 550 forms a closed shape. For example, point 575 can correspond to time 501A, 501B at the start of the cardiac contraction cycle and point 502A, 502B at the end of the cardiac contraction cycle. In an example, the shape can be constructed such that the shape forms an open shape (e.g., discontinuous), or a shape having multiple intersections. In an example, the shapes 550, 560 can be formed using data from a single cardiac contraction cycle, or a central tendency (e.g., mean, average, median) of the data over two or more cardiac contraction cycles. In an example, the signals 500, 530 can be measured continuously such as can form shapes 550, 560, or be sampled such as at two or more intervals, such as in a time-series. For example, a shape can be formed (e.g., such as using linear interpretation, curve fit, etc.) using the data sampled at the two or more intervals as discussed in FIG. 10.

In an example, the shapes 550, 560 can be compared such as to provide an indication of the physiological condition of the subject. In an example, a comparison of the shapes can include comparing one or more contraction metrics associated with the shapes 550, 560. For example, the processor 190 can be configured to compare shape area between one or more shapes or to a criterion. For example, the comparison of shape area to a criterion, can correspond to a change in the physiological condition of the subject, such as can be indicated by an increase to cardiac electromechanical delay (e.g., exceeding a threshold, differing from a reference by a specified amount, lying within or outside of a specified range of values, etc.). A comparison of the morphology over at least a corresponding portion of the shapes 550, 560 can indicate to a change to the subject's physiological condition. For example, the change to a portion associated with a ventricular contraction can correspond to an increased electromechanical delay, such as caused by myocardial ischemia to at least a portion of the heart.

FIG. 6 illustrates generally an illustrative example of a relationship between the magnitude of a response signal versus frequency. As described above, the IMD 105 can include a receiver circuit 115, for example, configured to receive a signal indicative of the motion of the implantable lead, such as the response signal, obtained in response to an excitation signal provided by the excitation circuit 110. In an example, the magnitude 600 of the response signal can vary as a function of frequency due the electrical characteristics of the implantable lead 145 over a specified frequency range. For example, a relatively stable or "flat" magnitude response (e.g., a magnitude value within a defined range) can result from the interaction of the electrical characteristics of the implantable lead 145 and the excitation signal in a first frequency range 605, such as between DC or near-DC (e.g., about 0 Hz) and a second frequency 615 (e.g., about 10 KHz), such as due to the resistive components of the lead impedances 350-360 having more influence than the capacitive, or inductive components. However, for an excitation signal within a second frequency range 607 (e.g., from about 50 MHz to about 150 MHz), the capacitive or inductive elements of the lead impedances 350-360 can dominate the response, such as causing the response signal magnitude 610 to decline as a function of frequency over the second frequency range 607.

In an example, the interaction of an excitation signal at a frequency, such as frequency 617, and the electrical characteristics of the implantable lead 145 can result in a response signal 620, such as having a magnitude 622. In an example, the electrical characteristics of the implantable lead 145 can result from inductive or capacitive coupling between portions of the implantable lead such as due to the position and or location of the implantable lead 145 within or near the heart. In an example, the motion of the heart, such as a cardiac contraction cycle, can result in corresponding motion of the implantable lead 145. In an example, the motion of the implantable lead can cause the electrical characteristics of the implantable lead 145 to vary as a function of time. For example, the motion of the implantable lead can cause the magnitude of the response signal to vary as a function of time over a specified frequency range. Such magnitude signals 640, 650, can result from the variance in the electrical characteristics due to motion of the implantable lead caused, at least in part, by motion of the heart 205.

In an example, an excitation signal at a frequency 617, such as can be provided by the excitation circuit 110, can interact with the time-varying electrical characteristics of the implantable lead 145, such as to provide a signal indicative of the motion of the implantable lead 145 (e.g., a response signal at least in part including an LMI signal 630). For example, the excitation signal at a frequency 617 can interact with the time-varying electrical characteristics of the implantable lead 145 during motion of the implantable lead. The motion of the implantable lead 145, such as caused a cardiac contraction cycle, can result in a response signal at a specified frequency having a time-varying magnitude value that can vary between a peak value 632A and a minimum value 634A. In an example, the response signal can include a carrier signal at the excitation frequency 617, and a modulating signal, such as a time-varying component resulting from the motion of the implantable lead (e.g., the LMI signal 630). For example, the magnitude of the LMI signal 630 can correspond to the time-varying magnitude of the response signal at the specified frequency such that the magnitude of the LMI signal 630 can vary between a peak value 632B and a minimum value 634B. In an example, the response signal can be conditioned such as to extract or otherwise provide the LMI signal for use by an analysis circuit, such as the arrhythmia classification circuit 120. Phase information can also be obtained, such as with respect to a reference phase corresponding to the excitation signal. Thus, the techniques above can be applied generally to magnitude or phase information, or to a real part or imaginary part of the response signal, in the case of a complex response signal.

Figure 7:
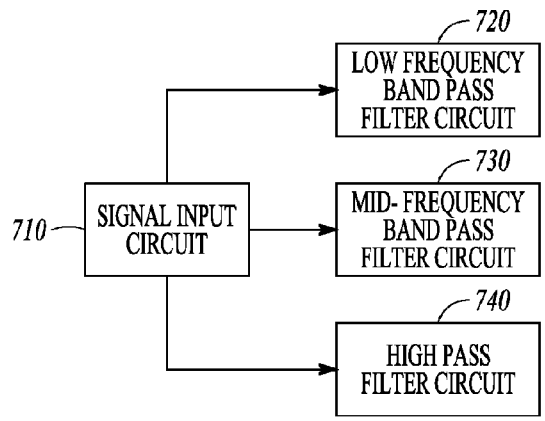
FIG. 7 illustrates generally an example of a system that can be used for conditioning a signal.

FIG. 7 illustrates generally an example of a system that can be used for conditioning a response signal for analysis. In an example, the receiver circuit 115 can include a signal input circuit 710, such as configured to receive a response signal from the implantable lead 145. In an example, the signal input circuit can include circuitry such as configured to provide, or otherwise obtain, the LMI signal from the response signal. For example, the LMI signal provide or otherwise obtained via demodulation, such as to remove a carrier frequency 617, such as to provide the LMI signal (e.g., via AM demodulation such as envelope detection or filtering, or via FM demodulation such as using a phase-locked loop, etc.). In an example, the LMI signal can include information about the motion of the implantable lead, such as caused by mechanical manipulation of the one or more leads caused by motion of at least one of the heart muscle, a heart valve, respiratory musculature, lungs, skeletal musculature, a variation in blood pressure, or other forces acting directly on the one or more leads.

In an example, the receiver circuit 115 can include one or more filters to provide information about one or more physiological conditions associated with the heart, such as information about the motion of the implantable lead in the LMI signal. In an example, the implantable lead 145 can be moved slowly, such as due to bending resulting from a cardiac contraction cycle. The implantable lead 145 can move quickly, such as caused by an impact on the lead resulting from a valve closure. In an example, the LMI signal can be filtered in one or more frequency ranges, such as to distinguish between one or more causes of the motion of the implantable lead. In an example, the receiver circuit 115 can include a low-frequency band pass filter circuit 720, a mid-frequency band pass filter circuit 730, or a high pass filter circuit 740. In an example, the filter circuits 720-740 can include a near-DC filter circuit, such as a high pass filter circuit configured to attenuate or remove signal noise under a frequency (e.g., about 0.05 Hz), configured to provide a baseline such as by filtering near-DC signal components. For example, the baseline can correspond to a near zero-energy or near-zero magnitude LMI signal when the implantable lead is not moving. In an example, the near-DC filter circuit can be included in one or more of the low-frequency band pass filter circuit 720, the mid-frequency band pass filter circuit 730, or the high pass filter circuit 740.

In an example, the low-frequency band pass filter circuit 720 can be configured to filter the LMI signal, for example, at a low frequency range (e.g., from about 0.05 Hz to about 10 Hz), such as to provide information indicative of the motion of the implantable lead 145, such as due to mechanical motion of the heart 205. For example, the low-frequency band pass 720 filter can provide a filtered LMI signal representative of the motion of the implantable lead due to motion caused by a cardiac contraction cycle. In an example, the filtered LMI signal can provide information representative of motion of the one or more implantable leads such as can be useful for verification of capture of a electrostimulation pulse, managing fusion in capture detection applications or CRT applications, or monitoring to detect a lead dislodgment. In an example, the filtered LMI signal can be used for monitoring myocardial contraction such as to manage a CRT therapy, to detect myocardial ischemia, to determine relative changes in stroke volume, or cardiac output, to detect abnormalities with relaxation of the cardiac muscle, or to detect abnormal mechanical contraction and to monitor electro-mechanical delay in the myocardium.

In an example, the mid-frequency band pass filter circuit 730 can be configured to filter the LMI signal, such as over a mid-frequency range (e.g., from about 0.05 Hz to about 30 Hz), such as to provide information indicative of the motion of the implantable lead 145, such as due to mechanical motion of the heart 205. For example, the mid-frequency band pass filter 730 can provide a filtered LMI signal representative of the motion of the implantable lead due to motion caused by a cardiac contraction cycle. For example, the filtered LMI signal can provide information useful for decompensation detection, rhythm discrimination using myocardial contraction morphology or myocardial contraction spectrum, to guide therapy to determine if ATP should be attempted before a shock, or to determine the timing of the shock, arrhythmia detection, or assessing autonomic function. In an example, the filtered LMI signal can be used to monitor the integrity of the implantable lead.

In an example, the high pass filter circuit 740 can be configured to filter the LMI signal, such as to filter signal out signal components under a specified frequency range (e.g., above about 10 Hz), such as to provide information indicative of the motion of the implantable lead 145, such as due to mechanical motion of the heart 205. For example, the mid-frequency band pass filter 730 can provide a filtered LMI signal representative of the motion of the implantable lead due to motion caused by one or more portions of the heart during a cardiac contraction cycle (e.g., a valve impact, frictional contact between cardiac muscle and the implantable lead, etc.). For example, the filtered LMI signal can provide information useful to detect heart sounds, or to detect the timing and amplitude of valve impact on leads. In an example, the filtered LMI signal can be used to detect lead maturity (e.g., a connection between myocardial tissue and the implantable lead 145), or lead dislodgement. In an example, the filtered LMI signal can be used for dyssynchrony measurement or CRT optimization, such as by detecting right side and left side heart sounds.

Figure 8:
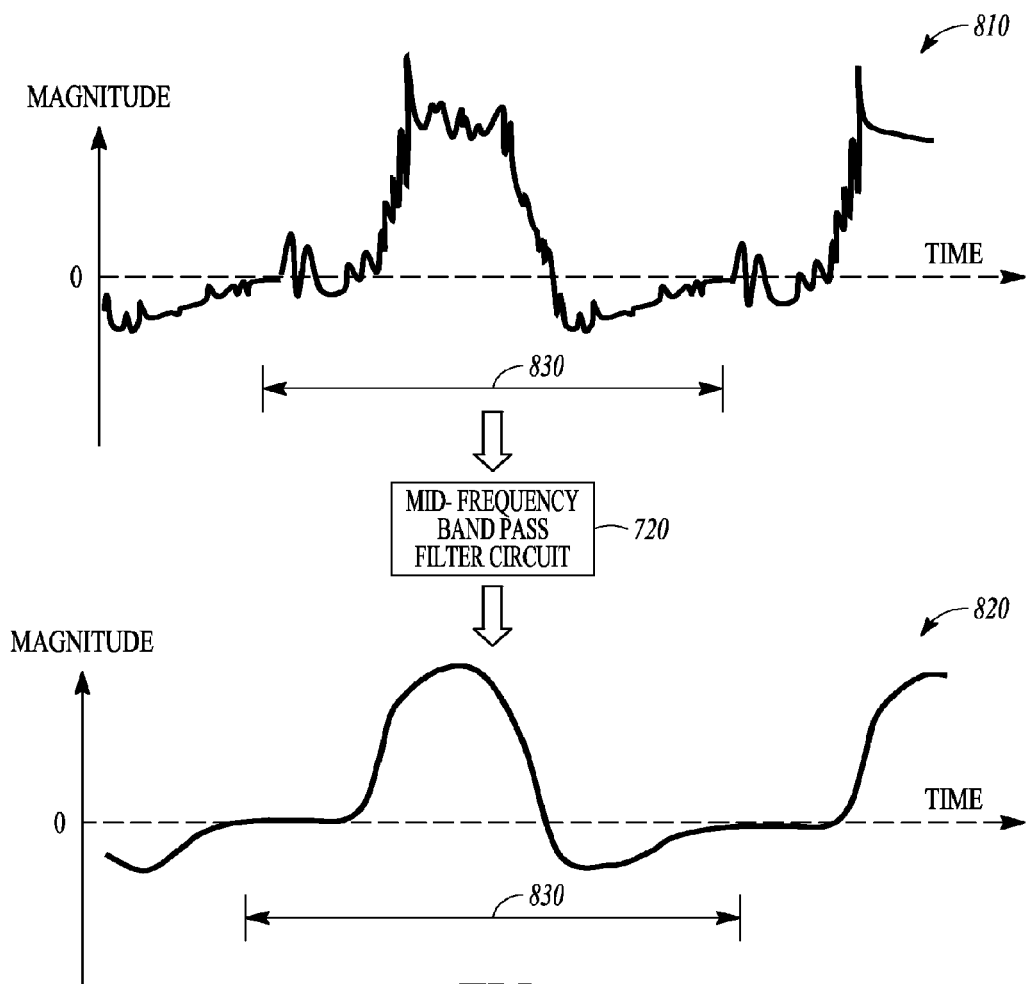
FIG. 8 illustrates generally an illustrative example that can include filtering or otherwise conditioning a response signal.

FIG. 8 illustrates generally an illustrative example that can include filtering or otherwise conditioning a response signal. In an example, an LMI signal can be obtained by the receiver circuit 115, such as can include an LMI signal indicative of the motion of the implantable lead 145, such as the LMI signal 810. In an example, the LMI signal 810 can be filtered, such as to provide information about the cardiac contraction cycle. For example, the LMI signal 810 can be filtered, such as by the low-frequency band pass filter 720, such as to provide a filtered LMI signal 820 such as a mechanical contraction waveform.

Figure 9:
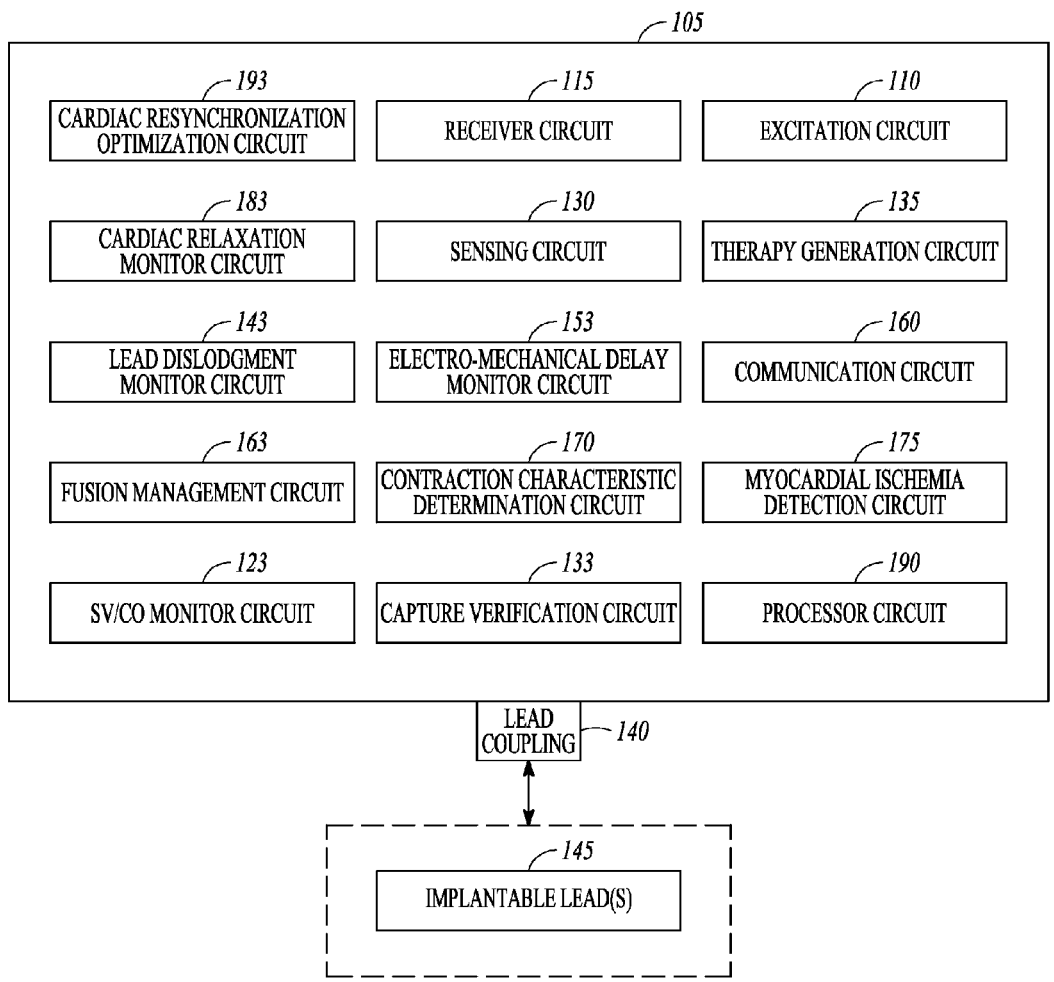
FIG. 9 illustrates generally an example of an ambulatory medical device that can be configured to analyze a signal indicative of the movement of the implantable lead.

FIG. 9 illustrates generally an example of an ambulatory medical device that can be configured to analyze a signal indicative of the movement of the implantable lead 145, such as for an indication of the movement of the heart 205 during a cardiac contraction cycle. In an example, the IMD 105 can include one or more of the excitation circuit 110, the receiver circuit 115, an arrhythmia detection circuit, an arrhythmia classification circuit, the sensing circuit 130, the therapy generation circuit 135, the lead interface connection 140, a communication circuit 160, the SV/CO monitor circuit 123, the capture verification circuit 133, the lead dislodgment monitor circuit 143, the electromechanical delay monitor circuit 153, the fusion management circuit 163, the myocardial ischemia detection circuit 173, the cardiac relaxation monitor circuit 183, the cardiac resynchronization optimization circuit 193, or a processor circuit 190.

Figure 10:
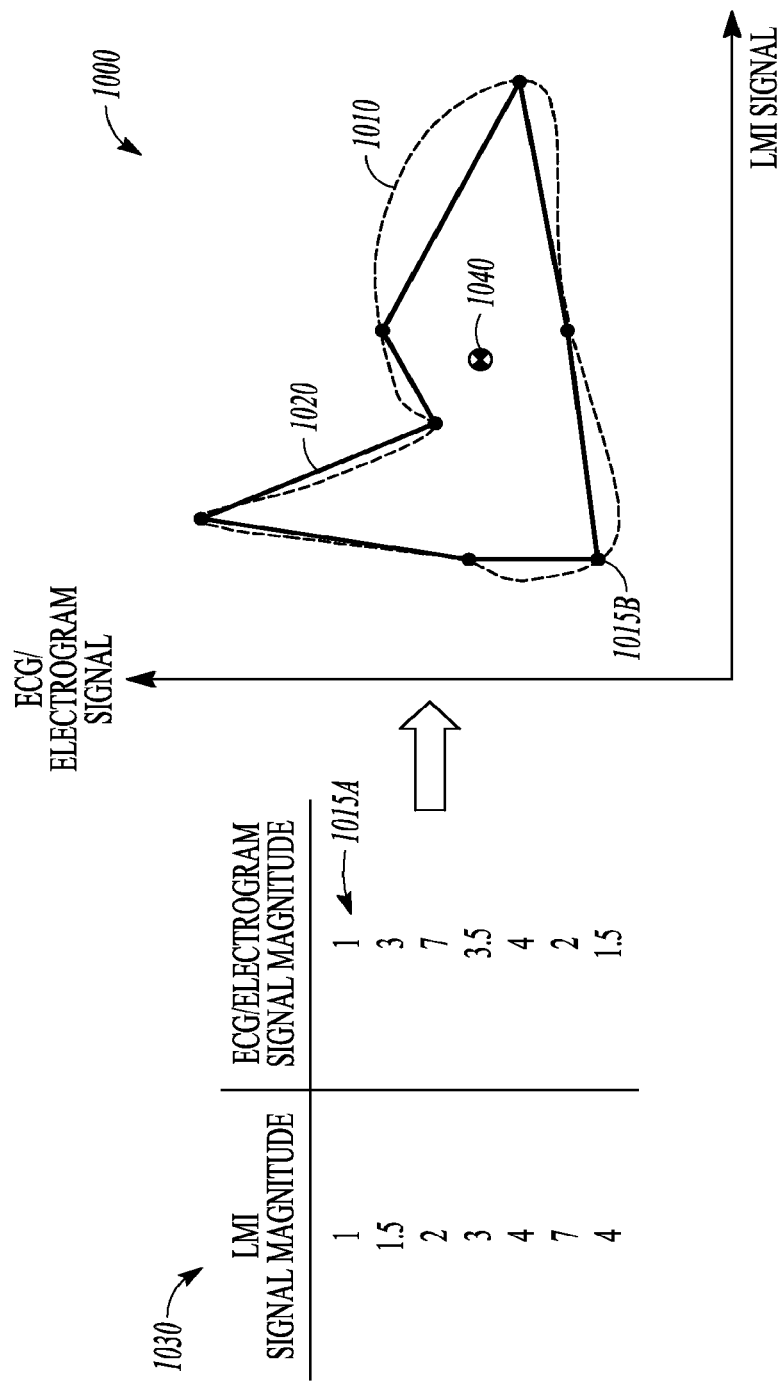
FIG. 10 illustrates generally an example of a relationship between a signal indicative of cardiac electrical activity and a signal indicative of the movement of the implantable lead.

FIG. 10 illustrates generally an example of a relationship between a signal indicative of cardiac electrical activity and a signal indicative of the movement of the implantable lead. As described above, the processor 190 can construct a template 1000 including a continuous two-dimensional shape (e.g., shape 560), or a two-dimensional shape illustrative of sampled data (e.g., shape 1020). In an example, shape 1020 can be constructed using a time-series 1030, where each entry in the time series can correspond to the relationship between at least a portion of the LMI signal and the electrogram. For example, the LMI signal and the electrogram can be aligned (e.g., to a time fiducial) such that element 1015A of time-series 1030, can correspond to a point 1015B on the shape 1020. In an example, the time-series 1030 can include three or more points, over at least a portion of a contraction cycle, indicative of the electromechanical activity of the heart. In an example, contraction metrics, such as an area, a curvature, or a central tendency (e.g., a centroid 1040), can be determined using one or more of the time-series 1030, or the shape 1020.

Figure 11:
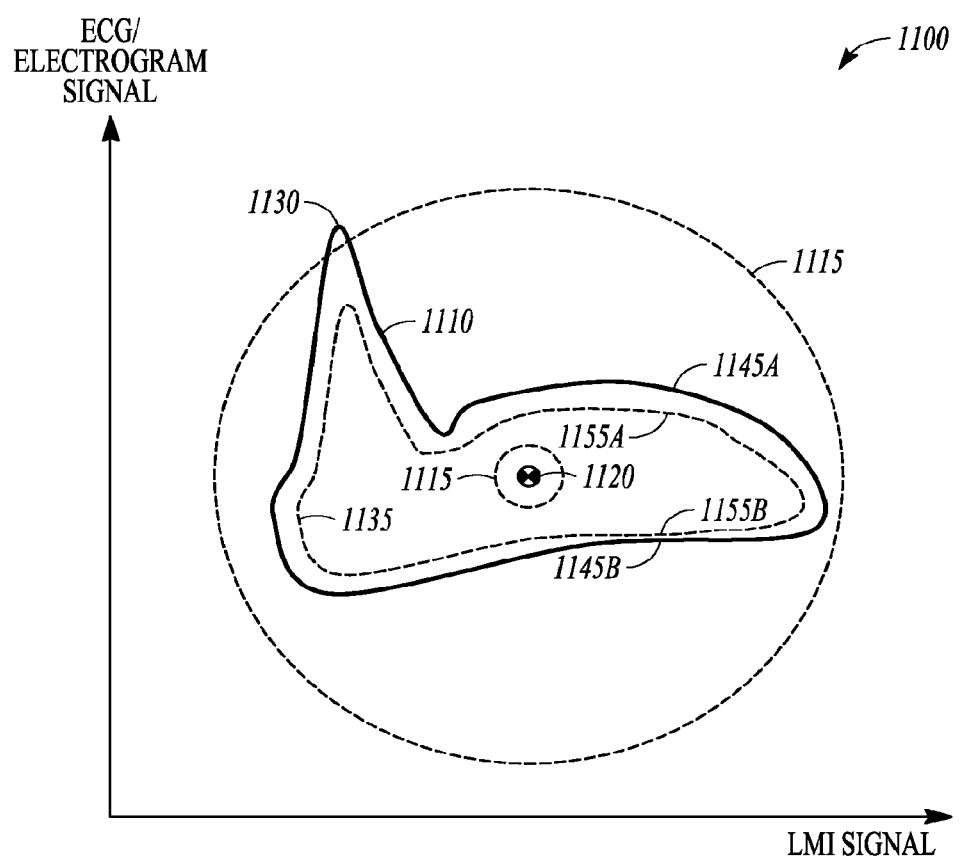
FIG. 11 illustrates generally an illustrative example of a comparison between a criterion and a contraction metric of the relationship between the signal indicative of cardiac electrical activity and the signal indicative of the movement of the implantable lead.

FIG. 11 illustrates generally an illustrative example of a comparison between a criterion and a contraction metric of a relationship between a signal indicative of cardiac electrical activity and a signal indicative of the movement of the implantable lead. In an example, a template 1100 can include a shape 1110 indicative of the electromechanical operation of the heart, such as the relationship between at least a portion of an electrogram and an LMI signal. As described above, one or more contraction metrics can be determined using the shape 1110. Examples of contraction metrics can include a centroid 1120, a morphological feature (e.g., peak 1130), or a curvature (e.g., the curvature 1140 between fiducial 1145A and 1155A).

In an example, the processor 190 can be configured to compare the one or more contraction metrics to one or more criteria. For example, the criteria can include threshold of a specified value (e.g., the threshold 1115), a specified range of values (e.g., such as the area between the criteria 1125, and 1135), or a reference curvature (e.g., the curvature between 1145B and 1155B). For example, the criterion can have a specified value (e.g., criterion 1115, 1125), such as a circle having a radius equal to that of the specified value. An example of a criterion (e.g., criterion 1135) can vary as a function of at least one of the signal indicative of electrical activity, or the LMI signal.

In an example, the processor 190 can indicate a change to the physiological condition of a subject (e.g., a change to electromechanical delay of the heart 205) when the contraction metric, such as the centroid 1120, exceeds a criterion (e.g., the threshold 1115). In an example, the processor 190 can indicate a change to the physiological condition of the subject (e.g., an increased cardiac relaxation time), such as when a feature (e.g., the peak 1130) of the shape 1110 is out of a specified range (e.g., the range of values between the criteria 1125, 1135). In an example, the processor 190 can indicate a change to the physiological condition of a subject (e.g., an indication of myocardial ischemia) when a contraction metric (e.g., the curvature between 1145A and 1155A) differs from the reference curvature between 1145B and 1155B by a specified amount.

Additional Examples

Generally, a healthy heart can provide at least two distinct heart sounds. The first sound, "S1," is typically produced by the closing of the atrioventricular valve leaflets. The second sound, "S2," is typically produced by the closing of the semilunar valve leaflets. In a clinical setting, these events can be detected such as through cardiac auscultation by an examiner, using a stethoscope.

In some individuals, various cardiac conditions can cause additional detectable mechanical vibrations, though these may or may not be audible to the examiner. For example, a heart murmur can occur when blood is flowing harder or faster than in an otherwise healthy individual. Such a murmur can indicate a serious heart problem or merely a benign cardiac event. In another example, an "S3" sound, also known as a protodiastolic gallop, can indicate a failing left ventricle. An "S4" sound, also known as presystolic gallop, can sometimes be detected in patients exhibiting restrictive cardiomyopathy.

In addition to vibrations or sounds indicative of heart function, blood flowing through blood vessels can also produce detectable vibrations useful for diagnosis and assessment of various medical conditions. The location, velocity, and pressure of blood flow are variables that can be assessed by detection of such vibration, among other variables. Thus, mechanical vibration monitoring capabilities can be included in an implantable or an ambulatory medical device, such as to store such information for later review or analysis, or to respond to such mechanical information. For example, an individual with an implantable medical device, such as a pacemaker, can benefit from mechanical vibration monitoring, including heart sound monitoring. Such monitoring can be used for diagnosis, or an initiation or adjustment of treatment. By identifying a mechanical vibration (e.g., including one or more heart sounds), therapy can be tailored to an individual's needs, or heart sound abnormalities can be provided to a caregiver for assessment or treatment.

Implantable acoustic and mechanical transducers can be used in detecting heart and blood mechanical vibrations (e.g., including one or more heart sounds). However, the resulting acoustic information from these transducers can produce a low signal level that can be degraded by extraneous noise. Furthermore, devices having a dedicated acoustic or mechanical transducer can require additional sensors within, on, or attached to the implantable or ambulatory device, such as resulting in a greater surface area, physical volume, or number of interconnects as compared to a comparable implantable device lacking such a dedicated acoustic or mechanical transducer.

The present inventor has recognized, among other things, that mechanical information indicative of cardiac, blood, or vascular motion can be detected using a motion of one or more conductors electrically coupled to the ambulatory or implantable device. For example, the present inventors have also recognized that an implantable lead electrically and mechanically tethered to an implantable or ambulatory medical device can provide information indicative of the motion of the lead, such as using one or more electrical measurements as described in the following examples, such as to detect cardiac, blood, or vascular motion. Such information indicative of motion can also be used to time or to verify the effectiveness of a cardiac therapy (e.g., electrostimulation), in addition to diagnosing one or more cardiac conditions.

An ambulatory medical device can include an excitation circuit configured to be electrically coupled to an implantable lead, the excitation circuit configured to provide a non-tissue-stimulating first signal to the implantable lead when the implantable lead is located at or near a tissue site. In an example, the system can include a detection circuit configured to be electrically coupled to the implantable lead and configured to receive a second signal, in response to the first signal, from the implantable lead, the second signal determined at least in part by a motion of the implantable lead.

Figure 12:
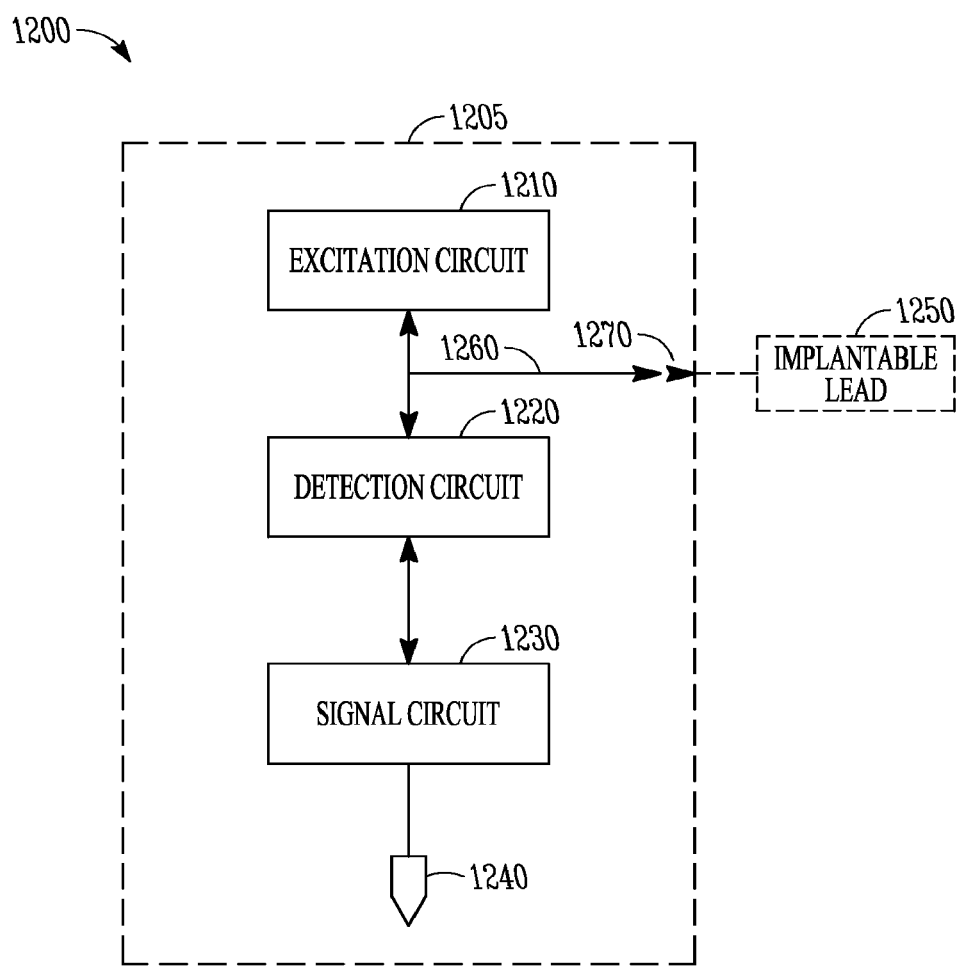
FIG. 12 illustrates generally an example of a system comprising an ambulatory medical device that can include an excitation circuit, a detection circuit, a coupling to an implantable lead, a signal processor, or an output.

FIG. 12 is a diagram illustrating generally an example of a system 1200 comprising an ambulatory medical device 1205 that can include an excitation circuit 1210, a detection circuit 1220, a signal processor 1230, an output 1240, an interconnect 1260, or a lead coupling 1270. In an example, an implantable lead 1250 can be coupled to the lead coupling 1270. One or more of the excitation circuit 1210, detection circuit 1220, signal processor 1230, output 1240, or interconnect 1260 can be realized on or within a commonly shared substrate, such as on a commonly-shared integrated circuit, module, circuit board, or the like. In another example, each block can be included in a physically separate ambulatory device, such devices coupled as shown in the example of FIG. 12, such as using one or more wired or wireless communicative couplings.

In the example of FIG. 12, the ambulatory medical device 1205 can include a cardiac stimulator, such as including pacing or cardiac resynchronization therapy (CRT) circuitry configured to deliver pacing or resynchronization energies to cardiac tissue. In an example, the ambulatory medical device 1205 can include a neural stimulator device, such as to provide electrical, mechanical, optical, acoustic or chemical stimulation to one or more neural targets.

In the example of FIG. 12, the excitation circuit 1210 can be coupled to a detection circuit 1220. The excitation circuit 1210 generally provides an excitation energy, such as including a first signal. In an example, the first signal can include an oscillating electrical signal, such as a time-varying voltage or current. In an example, the first signal can include a pulsed electrical signal, such as including one or more current or voltage pulses including a specified amplitude, duration, pulse repetition rate, duty cycle, or morphology, among other parameters. In an example, the excitation circuit 1210 can be coupled to the lead coupling 1270 via interconnect 1260, such as using a header or other connector included as a portion, part, or component of the ambulatory medical device 1205.

In the example of FIG. 12, an implantable lead 1250 can be coupled to the lead coupling 1270. For example, the implantable lead 1250 can include one or more conductors. In an example, the implantable lead 1250, such as coupled to the implantable lead coupling 1270, can be located at a site within or on the body (e.g., including one or more surface, subcutaneous, or intravascularly-located electrodes or conductors). In an example, the implantable lead 1250 can be implanted or otherwise place within a body, such as within or near a heart, either temporarily or more permanently, such as for ambulatory monitoring or therapy delivery.

In the example of FIG. 12, the detection circuit 1220 can be coupled both to a signal processor 1230 and the lead coupling 1270 via a commonly-shared interconnect 1260. In an example, the implantable lead 1250, or an external lead, can be coupled to the lead coupling 1270. In an example, the detection circuit 1220 can be configured to receive a second signal provided by the implantable lead 1250. For example, the detection circuit 1220 can be configured to interpret or processes the first signal, such as by providing the first signal to the implantable lead 1250 before or during receiving the second signal.

In the example of FIG. 12, the detection circuit 1220 can be configured to receive a second signal, such as from the implantable lead 1250 via the lead coupling 1270 and the interconnect 1260 (e.g., in response to the first signal). In an example, the detection circuit 1220 can be configured to interpret and process a received second signal before transmitting the received second signal to the signal processor 1230. For example, the detection circuit 1220 can be configured to determine a first characteristic of the second signal (e.g., information about an amplitude, frequency, noise floor, signal-to-noise ratio, or one or more other characteristics). In an example, the amplitude characteristic of the second signal can be compared to a threshold value, and the result of the comparison can be used to determine if the received second signal can be further processed by the signal processor 1230. For example, if the amplitude of the second signal meets or exceeds a threshold value, the detection circuit 1220 can be configured to transmit the second signal to the signal processor 1230 for further analysis. Conversely, if the amplitude of the second signal is below the threshold value, the detection circuit can withhold transmission of the second signal or otherwise indicate to the signal processor 1230 that further analysis should be withheld (e.g., if the second signal is so low in amplitude that extraction of motion information would be difficult).

In the example of FIG. 12, the signal processor 1230 can be coupled to the detection circuit 1220 and the output 1240. In an example, the signal processor 1230 can be configured to receive information derived from the second signal. The signal processor 1230 can be configured to extract from the second signal information indicative of motion of the implantable lead 1250. Such motion of the implantable lead 1250 can include a physical displacement of any constituent element of implantable lead 1250 with respect to an equilibrium position. In an illustrative example, the implantable lead 1250 can experience a physical displacement because the implantable lead is mechanically coupled to a vibrating tissue, such as implanted within or near contractile tissue in the heart. In an example, the information indicative of motion of the implantable lead 1250 can include audible or acoustic information such as provided by a heart sound, or other higher or lower-frequency mechanical information not necessarily within the audible frequency spectrum.

In an example, information indicative of motion of the implantable lead 1250 can include impedance information, such as including a change in lead impedance determined at least in part by mechanically coupling cardiac or vascular mechanical vibrations to the implantable lead 1250. For example, impedance information can be interpreted by the signal processor 1230 to detect, classify, or monitor one or more physiological events. Such physiological events can include the closing of the atrioventricular or semilunar valve leaflets in the heart.

In the example of FIG. 12, the output 1240 can be coupled to the signal processor 1230. In an example, the output 1240 can receive information from the signal processor 1230. The received information can be passed through an output 1240 to one or more other portions, parts, or components of the ambulatory medical device 1205. In an example, the output 1240 can be coupled to another device via a wired or wireless communicative connection (e.g., to transfer information to one or more other implantable or ambulatory devices, or to an external assembly). In an example, the signal processor 1230 can perform one or more signal adjustments such as impedance or level adjustments, among others, before providing the lead motion information to the one or more other portions via the output 1240.

Figure 13:
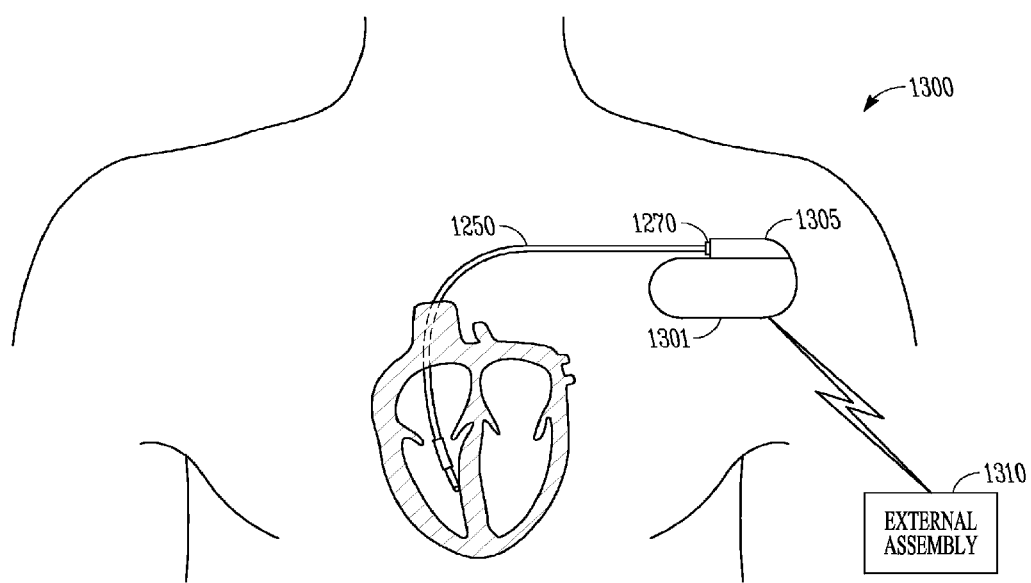
FIG. 13 illustrates generally an example of a portion of a system that can include an implantable medical device, an implantable lead, or a communicative coupling between the implantable medical device and an external assembly.

FIG. 13 illustrates generally an example of a system 1300 that can include an implantable medical device 1305. In this example, the implantable medical device 1305 can include one or more implantable lead couplings, such as a lead coupling 1270. In certain examples, the implantable medical device 1305 includes a hermetically-sealed or similar housing 1301 coupled to the implantable lead coupling 1270. For example, the housing 1301 can include titanium or other biocompatible material, such as one or more other conductive materials.

In the example of FIG. 13, the system 1300 can include an implantable lead 1250 implanted in a heart, such as implanted endocardially via an intravascular route from one or more of a subclavian vein or a femoral artery. In an example, the implantable lead 1250 can include one or more conductors, such as one or more concentric or laterally-separated conductors. In an example, one or more conductors can include a braided or coiled shield conductor. The one or more conductors can be insulated from one another and from the environment surrounding the implantable lead 1250, such as using a silicone or a poly-ether-ether-ketone (PEEK) insulation, among others. In an example, the conductors to be used for mechanical vibration sensing can be selected based on measurement of RF coupling or an AC impedance between the conductors. Such RF coupling or impedance measurements can be used to determine a conductor pair or combination likely to exhibit higher mechanical vibration sensitivity than other pairs or combinations. Such measurements can also be used to find a conductor pair or combination including an input impedance most closely matched to a conjugate of the output impedance of one or more of a detection circuit, excitation circuit, or interconnect as shown in FIG. 12, and FIGS. 14-16.

In an example, the implantable medical device 1305 can be configured to communicate with the external assembly 1310. The communication between the implantable medical device 1305 and an external assembly 1310 can be wireless or through a wired connection, or using one or more other communication schemes (e.g., using an optical communication link or an acoustic communication link, among others). For example, the external assembly 1310 can be a portion or part of a patient management system, such as including or in communication with one or more remote or web-based clients communicatively coupled to one or more servers comprising medical and patient databases.

In an example, the implantable medical device can include one or more of a pacemaker, a defibrillator, an implantable monitor, a drug delivery device, a cardiac resynchronization therapy device, a neural stimulation device, or one or more other implantable assemblies configured to monitor a person or configured to provide one or more treatments to the person. Such monitoring or treatment can include, among others, electrostimulation of tissue such as cardiac tissue, or electrical monitoring of muscular or cardiac activity, among others.

Figure 14:
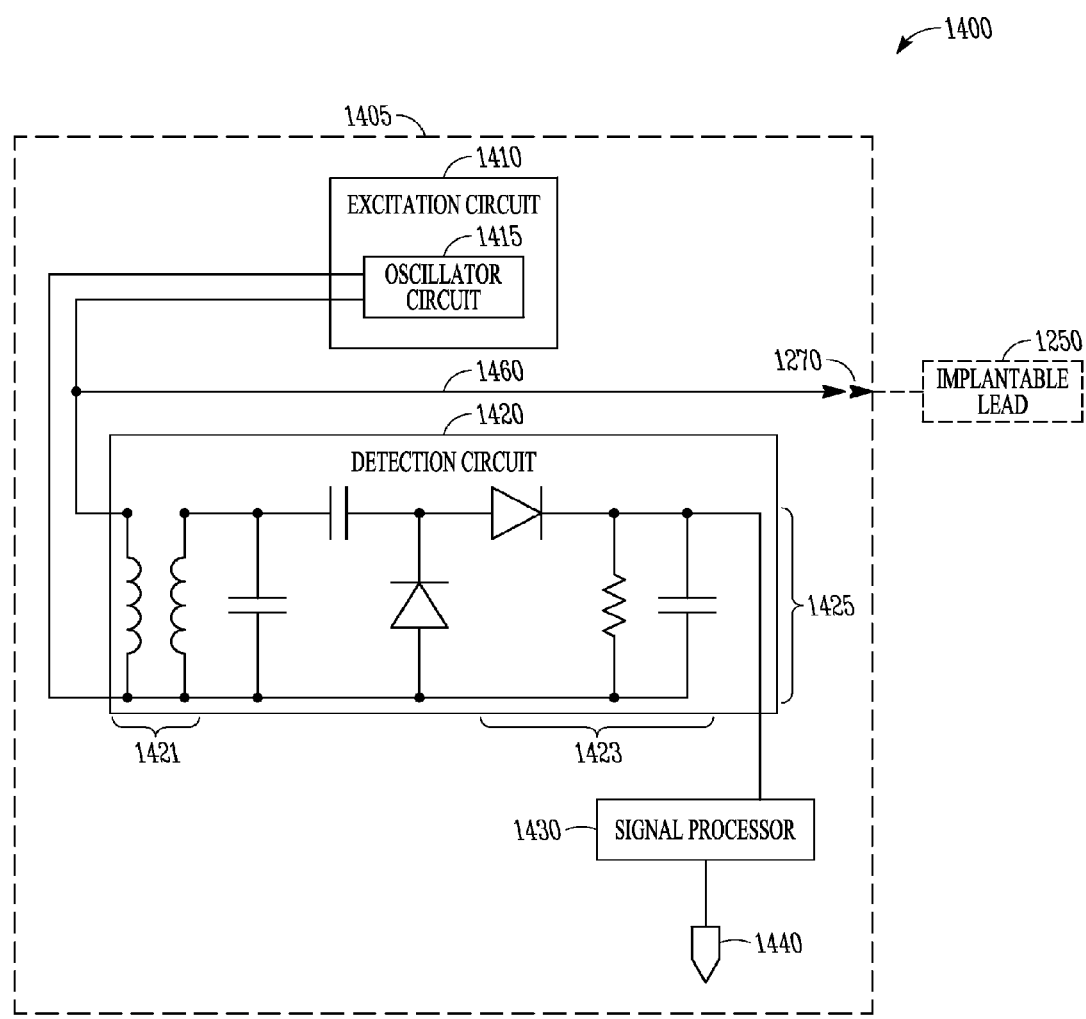
FIG. 14 illustrates generally an example of a portion of a system comprising an excitation circuit that can include an oscillator circuit, a detection circuit, a coupling to an implantable lead, a signal processor circuit, or an output.

FIG. 14 illustrates generally an example of a system 1400 that can include an ambulatory medical device 1405, such as including an implantable device as shown in the example of FIG. 13, an externally-worn assembly, or a combination of implantable and external portions. In this example, an excitation circuit 1410 can include an oscillator circuit 1415 such as configured to provide a first signal. In an example, the oscillator circuit can provide an RF signal (e.g. from about 10 to about 30 MHz), such as including a specified current level.

In an example, an interconnect 1460 can be coupled to one or more of the excitation circuit 1410 or a detection circuit 1420. In this example, the first signal (e.g., an excitation current signal) can be provided by the excitation circuit 1410 to develop a voltage across two conductors included in the lead coupling 1270 via the interconnect 1460. For example, the first signal can include one or more current signals provided to one of the conductors, and received from the other conductor. The detection circuit 1420 can be configured to receive a second signal (e.g. a developed voltage) across the lead coupling 1270.

In an example, the detection circuit 1420 can include a demodulation circuit 1425. The demodulation circuit 1425 can include an envelope detector 1423 or a tuned resonant transformer 1421 that can be impedance-matched to one or more other attached components. In an example, the envelope detector 1423 can demodulate or extract a relatively low frequency component of time-varying voltage from the second signal, such as containing information indicative of motion of an implantable lead 1250 attached to the lead coupling 1270. The demodulation circuit 1425 can be coupled to a signal processor 1430. In an example, the signal processor 1430 can be configured to extract information indicative of motion of the implantable lead 1250, such as including protodiastolic or presystolic gallop sounds, or other mechanical vibrations such as indicative of blood flow, or pressure, among others.

In an example, additional elements can be included in the system 1400 to enhance sensitivity or provide additional mechanical event information. For example, multiple implantable leads can be implanted in multiple locations within or on a body and lead motion information can be collected from one or more of the multiple locations. For example, a second lead comprising at least one electrical conductor can be coupled to a second lead coupling, or the implantable lead 1250 can include multiple electrical conductors that can be coupled to one or more lead couplings. In an example, one or more mechanical events can provide a change in the impedance of the system comprising the multiple conductors, such as detectable using the second signal provided in response to the first signal. In an example, the signal processor 1430 can be coupled to an output 1440, and extracted information indicative of motion of the implantable lead 1250 can be communicated to another assembly via the output 1440. Such other assemblies can include, among others, an additional ambulatory medical device located internally or externally to a body, or an external assembly 1310, a combination of one or more implantable and external assemblies.

Figure 15:
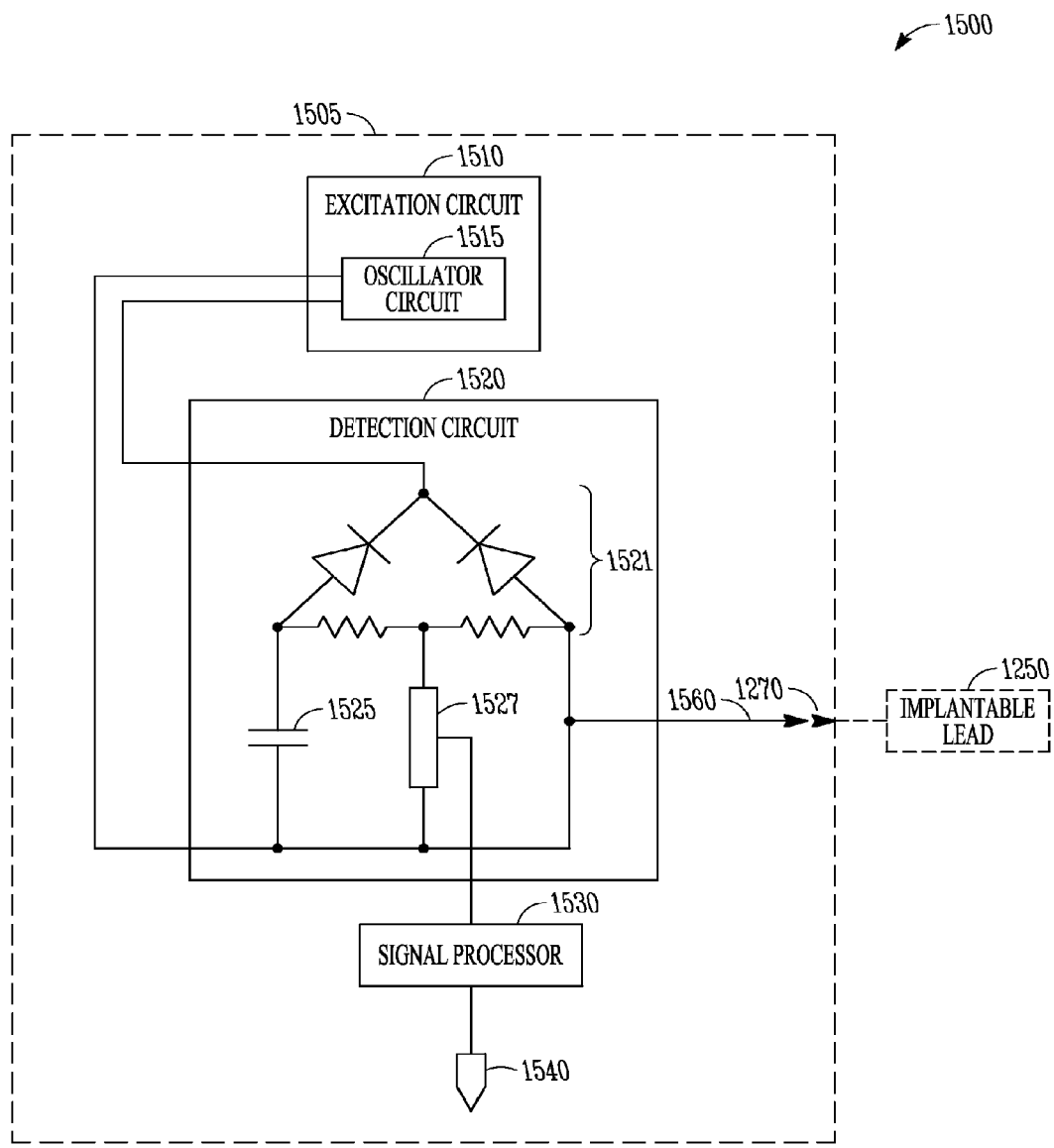
FIG. 15 illustrates generally an example of a portion of a system comprising an excitation circuit that can include an oscillator circuit, a detection circuit comprising a coupling to an implantable lead and a bridge circuit, a signal processor circuit, or an output.

FIG. 15 illustrates generally an example of a system 1500 including ambulatory medical device 1505, such as including an implantable device as shown in the example of FIG. 13, an externally-worn assembly, or a combination of implantable and external assemblies. In this example, an excitation circuit 1510 can include an oscillator circuit 1515 configured to provide a first signal, such as provided to a portion of a detection circuit 1520. In an example, an interconnect 1560 can be coupled to the detection circuit 1520. The detection circuit 1520 can include a bridge circuit 1521, a capacitive element 1525, or an envelope detector 1527, among other components or portions. In the example of FIG. 15, the sensitivity of detection circuit 1520 can vary with respect to a specified excitation frequency. In an illustrative example, the oscillator circuit 1515 can provide a first signal including a sine wave signal with a frequency of around 100 KHz to 1 MHz (or including one or more other frequencies). The bridge circuit 1521 can include one or more diodes or other rectifiers exhibiting low forward resistance, such as one or more germanium diode (e.g. type 1N60). In this example, the bridge circuit 1521 can include resistors of about the same values. The implantable lead 1250 can provide a capacitance, and the capacitive element 1525 can include a specified capacitance value approximately equal to the capacitance provided by the implantable lead 1250 when implantable lead 1250 is in equilibrium (e.g., relatively motionless, or subject to a specified baseline of vibration or motion). The capacitance provided by the implantable lead 1250 can be one or more capacitances provided between two or more conductors, such as included in a single implantable lead 1250, or between conductors respectively included in two or more implantable leads. Generally, the one or more capacitances can be provided by a combination of multiple conductors, and such capacitances can be combined in a series or parallel configuration, such as each including a capacitance contribution from one or more pairs of conductors. In an example, the capacitance can be provided between conductors of physically separate implantable leads. Such lead capacitance can vary in proportion or with respect to motion or vibration coupled to the lead such as from surrounding tissue or blood motion. In an example, the envelope detector 1527 can include a relatively high input impedance to achieve a specified sensitivity of the system 1500. The envelope detector 1527 can include one or more of a diode or rectifier detector, or a synchronous detector, such as to improve noise rejection, selectivity, or one or more other characteristics.

In an example, a signal processor 1530 can be configured to receive a signal from the detection circuit 1520, such as provided at least in part by the envelope detector 1527. For example, the signal processor 1530 can be configured to extract information from the received voltage signal indicating a motion of an implantable lead 1250. In an example, the signal processor 1530 can include a low pass filter circuit to process the signal received from the detection circuit 1520. In an example, the signal processor 1530 includes an amplification circuit, or one or more other circuits or components, such as to amplify the received signal. In an example, the signal processor 1530 can include an analog-to-digital converter to convert the information indicative of motion into a digital data signal, such as for storage, further processing, or for presentation to a caregiver or clinician.

In an example, an output 1540 can be configured to receive a signal from the signal processor 1530, and the output 1540 can be configured to transfer the information indicative of motion of the implantable lead 1250 to another implantable or ambulatory medical device, or to an external assembly such as the external assembly 1310 using a wireless or wired communicative coupling. In an example, the output 1540 can be configured to communicate with one or more external assemblies including one or more tabletop or handheld electronic devices (e.g. a cell phone, smart phone, tablet, laptop, or personal digital assistant (PDA), among others), in addition to or instead of one or more external assemblies dedicated for medical diagnosis or assessment.

In an illustrative example, one or more of the detection circuit 1520 or the signal processor 1530 can receive a second signal in response to the first signal, and the second signal can include a portion in-phase with the first signal, and a second portion in quadrature (e.g., ninety degrees out of phase) with the first signal. In this illustrative example, the detection circuit 1520 or the signal processor 1530 can use the quadrature component of the second signal to determine the change in capacitance of the lead system, thus canceling out the effect of the resistive component of an impedance presented by the implantable lead 1250 to the measurement circuit.

Figure 16:
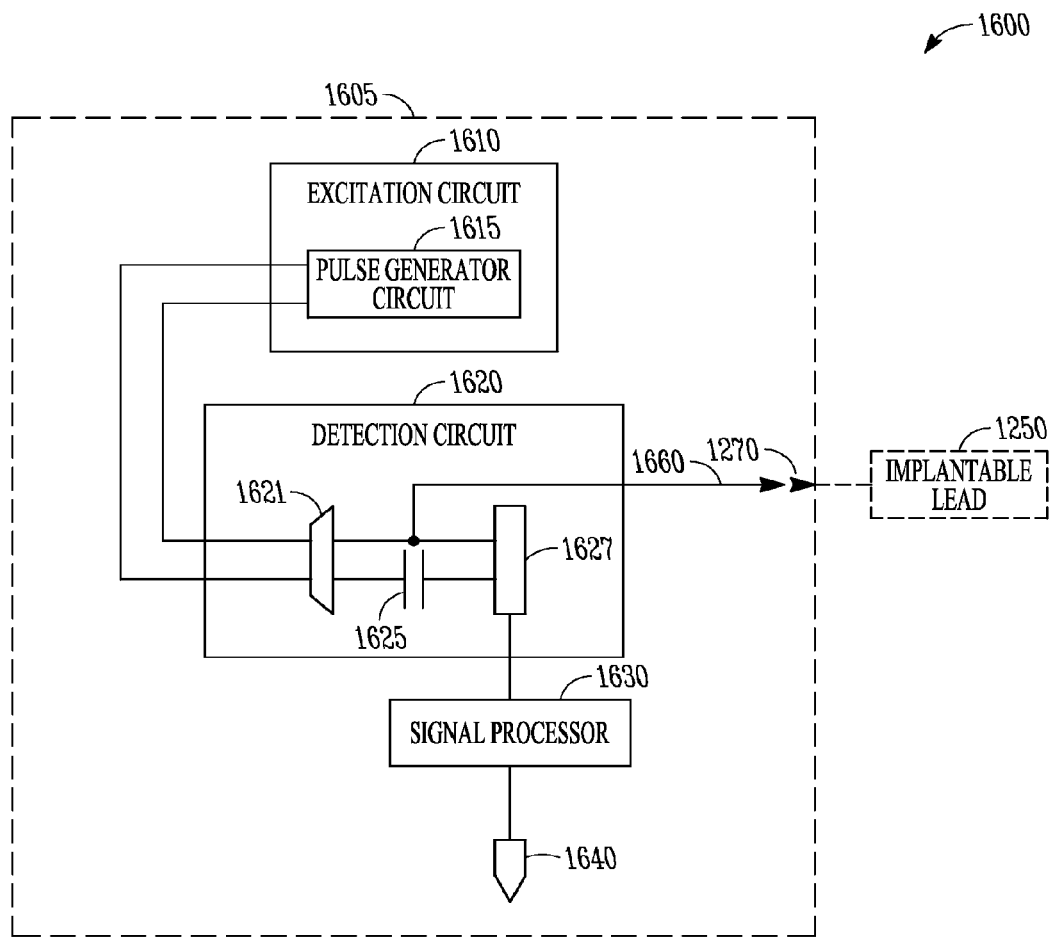
FIG. 16 illustrates generally an example of a portion of a system that can include an excitation circuit such as including a pulse generator circuit, a detection circuit including a coupling to an implantable lead and a voltage detector, a signal processor circuit, or an output.

FIG. 16 illustrates generally an example of a system 1600 including ambulatory medical device 1605, such as including an implantable device as shown in the example of FIG. 13, or an externally-worn assembly. In this example, an excitation circuit 1610 can include a pulse generator circuit 1615 configured to provide a first signal, and a detection circuit 1620. In an example, the detection circuit 1620 can include a multiplexer 1621, a capacitive element 1625, or a voltage detector 1627. In an example, the multiplexer 1621 can be configured to select among one or more inputs, wherein the inputs can be coupled to the excitation circuit 1610, or another signal-generating source. In an example, the multiplexer 1621 can be under the control of the detection circuit 1620 or another component of the ambulatory medical device 1605. An interconnect 1660, the voltage detector 1627, or a lead coupling 1270, among other components, can be coupled to the multiplexer 1621.

One or more portions of the system 1600, such as the interconnect 1660, multiplexer 1621, or voltage detector 1627, can be implemented on a rigid or flexible circuit board, such as including one or more application specific integrated circuits, among other components. In an example, the lead coupling 1270 can be implemented via an electrical and mechanical interconnect in a header block that can be attached to the housing 1301 of an implantable medical device housing, such as shown in FIG. 13. The housing 1301 of the implantable medical device itself can be used as one of the conductors for capacitance or impedance measurement.

In an example, the excitation circuit 1610 can be coupled to the multiplexer 1621. In an example, the multiplexer 1621 can be configured to couple the excitation circuit 1610 to each of the interconnect 1660 and the capacitive element 1625, concurrently or successively. In an example, the concurrent or successive coupling can be performed by the multiplexer 1621 under the direction of a logic circuit included as a portion of the detection circuit 1620. For example, the logic circuit can include a counter or timer such as to provide one or more counts or durations to be used by the logic circuit to switch the state of the multiplexer 1621, such as after a specified duration of time elapses as indicated by the counter or timer. In an example, the logic circuit can be configured to count a number of pulses provided by the excitation circuit 1610. In this example, the logic circuit can be configured to switch the state of the multiplexer 1621, such as after a specified count of a number of pulses is met or exceeded as indicated by the counter.

In the example of FIG. 16, the multiplexer 1621 can be configured to couple the first signal to a first capacitance provided by implantable lead 1250. In an example, a first voltage can be developed across the first capacitance in response to the first signal. A second signal that includes the first voltage can be received by the voltage detector 1627. In this example, a signal processor 1630 can receive the output of the voltage detector 1627. In an example, the signal processor 1630 can be configured to compare the received signal from the first capacitance to a threshold voltage (e.g., monitoring a charging of the first capacitance to reach the specified threshold voltage).

In the example of FIG. 16, the multiplexer 1621 can be configured to couple the first signal to a second capacitance provided by the capacitive element 1625 (e.g., a "reference capacitance," charged using the same or a similar first signal). In an example, the multiplexer 1621 can be configured to provide the first signal to each of the first capacitance and second capacitance, either separately, sequentially, or in combination. In an example, a second voltage can be developed across the second capacitance in response to the first signal. In an example, the second signal that includes the second voltage can be received by the voltage detector 1627. In this example, a signal processor 1630 can receive the output of the voltage detector 1627. In an example, the signal processor 1630 can be configured to compare the received signal from the second capacitance to the specified threshold voltage (e.g., monitoring a charging of the second "reference" capacitance to reach the specified threshold voltage).

In the example of FIG. 16, the signal processor 1630 can be configured to determine a relative indication of information (e.g., a ratio, a difference, etc.) derived from one or more of the first or second voltages measured with respect to the first or second capacitances. Coupling of mechanical vibration to the implantable lead 1250, or other motion of the lead, can cause a detectable change in the capacitance of the lead. For example, the second signal received from the first capacitance can differ from the second signal received from the second capacitance in response to a similar excitation by the first signal. In this manner, a variation between a reference capacitance (e.g., provided by capacitive element 1625) and the capacitance of the lead can be used to provide information corresponding to motion of the implantable lead. In an example, capacitive element 1625 can include, among other things, an additional specified capacitance such as provided by a discrete capacitor, a second implantable lead, or combination of conductors, a number of interconnected implantable leads, or a capacitive transducer.

In the example of FIG. 16, the first signal can charge the first capacitance to a first specified threshold voltage, and a corresponding duration of the charge time can be determined (e.g., such as when the first capacitance is charged using a sequence of current pulses or a constant current). In an example, the voltage detector 1627 can be configured to receive the first voltage in response to the charging of the first capacitance. In this example, the signal processor 1630 can be configured to determine a duration of a first charge time, corresponding to a duration where the first voltage is between a lower threshold (e.g., around 0 Volts), and an upper threshold (e.g., the first specified voltage threshold). In an example, the signal processor 1630 can be configured to determine a duration of a second charge time, corresponding to a duration where the second voltage is between the lower and upper thresholds. If the capacitance of the capacitive element 1625 and the lead capacitance are roughly equal, the determined first and second charge times can be roughly equal, such as when the lead 1250 is at rest or equilibrium.

In the example of FIG. 16, the excitation signal (e.g., the first signal), can include a series of current pulses having a specified peak current level, duration, pulse repetition rate, duty cycle, etc. The signal processor 1630 can be configured to count a number of pulses delivered to the lead 1250, or to a capacitive element 1625. For example, the voltage detector 1627 can be configured to receive pulsed signals and the signal processor 1630 can be configured to count the received pulsed signals. In an example, the signal processor 1630 can be configured to count a first count of a number of pulses provided to the first capacitance, such as to reach the specified threshold voltage (e.g., the pulse count can be a proxy for a measurement of a charge time duration, such as when pulses of determinable width and level are used). In an example, the signal processor 1630 can be configured to extract from the first count an indication of lead motion, since the variation in the lead capacitance can provide a difference in a number of pulses needed to reach the specified threshold, such as compared with a baseline number of pulses corresponding to a lead at rest or in equilibrium.

In an example, the sensitivity of the system 1600 can be enhanced by using a comparison between a second capacitance (e.g., a reference capacitance or another pair or combination of lead conductors) and the capacitance of the lead 1250. The signal processor 1630 can be configured to count a second count of a number of pulses provided to the second capacitance (e.g., using a series of pulses of determinable width or level, as above). For example, the signal processor 1630 can be configured to extract from the first and second counts a relative indication of information that can indicate lead motion (e.g., a difference, or ratio, etc., between the first and second counts of pulses). In an illustrative example, the signal processor 1630 can measure multiple pulse durations and perform comparison operations, such as including using one or more techniques disclosed in Pelletier et al. U.S. Pat. No. 4,011,500 entitled "PHYSICAL DISPLACEMENT SENSING WITH DIFFERENTIAL CAPACITOR," which is hereby incorporated by reference in its entirety, including its disclosure of using a differential capacitor to detect a physical displacement.

In an example, an output 1640 can be configured to receive information from the signal processor 1630, and to transfer such information to one or more other portions of the ambulatory medical device 1605, or to communicate with an external assembly.

Figure 17:
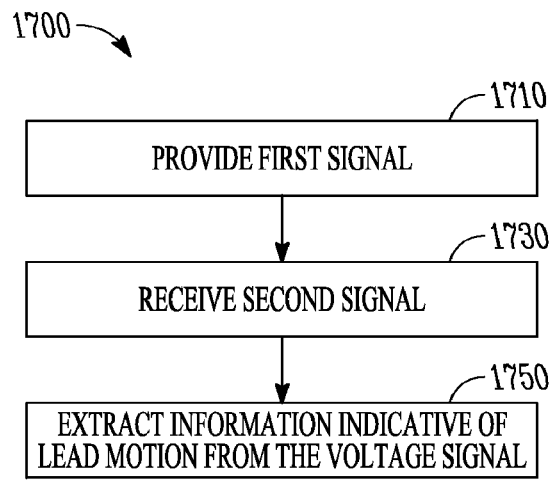
FIG. 17 illustrates generally an example that can include providing a first signal, receiving a second signal, or extracting information indicative of lead motion from the second signal.

FIG. 17 illustrates generally an example 1700 that can include providing a first signal, receiving a second signal, or extracting information indicative of lead motion from the second signal, such as using circuitry or techniques as discussed above in the examples of FIGS. 12-16.

At 1710, a first signal can be provided to excite the ambulatory medical device 1205. In an example, the first signal can be a non-tissue-stimulating electrical signal. For example, the first signal can be an AC signal generated or provided by an excitation circuit 1210. In an example, the first signal can be provided to an implantable lead 1250.

At 1730, a second signal can be received in response to the first signal. In an example, the detection circuit 1220 can be configured to receive the second signal from the implantable lead 1250. In an example, the second signal can include, among other signals, a phase-shifted or modulated version of the first signal, a voltage signal, a logic signal, or a data signal including information indicative of motion of the implantable lead.

At 1750, information can be extracted from the second signal. The extracted information can indicate motion of the implantable lead 1250. In an example, the information can indicate a relative or absolute indication of a displacement of the implantable lead 1250. In an example, the information can include an electrical representation of mechanical vibration or motion coupled to the lead, such as including a heart sound, a blood pressure sound, or respiratory sound, among others.

Figure 18:
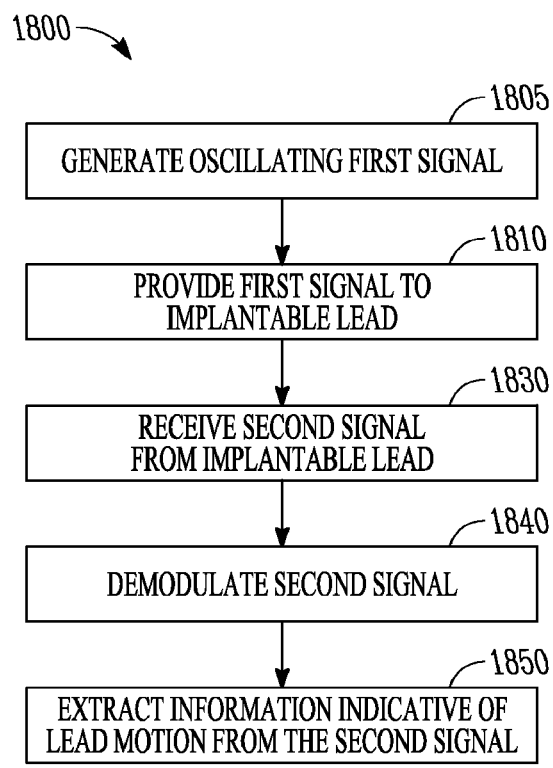
FIG. 18 illustrates generally an example that can include generating an oscillating first signal, providing the first signal to an implantable lead, receiving a second signal from the implantable lead, demodulating the second signal, or extracting information indicative of lead motion from the second signal.

FIG. 18 illustrates generally an example 1800 that can include generating an oscillating first signal, providing the first signal to an implantable lead, receiving a second signal from the implantable lead, demodulating the second signal, or extracting information indicative of lead motion, such as using circuitry or techniques discussed above with respect to FIGS. 12-16.

At 1805, a first signal can be generated by an oscillator circuit included in an excitation circuit 1210. In an example, the oscillator circuit can include a Colpitts oscillator. In an example, the first signal can include an AC signal and the frequency of oscillation can be tunable such as to achieve a specified sensitivity.

At 1810, the first signal can be provided to the implantable lead 1250, such as via an interconnect 1460 and a lead coupling 1270. In an example, the first signal can be coupled through a series capacitor with high DC or near-DC impedance to create a relatively constant current signal into the implantable lead 1250. In an example, a change in capacitance of the implantable lead 1250 can modulate the impedance of the circuit comprising the implantable lead 1250, the lead coupling 1270, and the interconnect 1460.

At 1830, a second signal can be received from the implantable lead 1250, such as in response to the first signal. In an example, the modulated impedance of the circuit comprising the implantable lead 1250, the lead coupling 1270, and the interconnect 1460 can produce the second signal in response to the first signal such that the second signal can be different than the first signal.

At 1840, the second signal can be demodulated to recover the information indicative of lead motion. In an example, the second signal can be received by a detection circuit 1420 wherein a demodulation circuit 1425 can be used to demodulate the received second signal. The demodulation circuit 1425 can include a tuned resonant transformer 1421 or an envelope detector 1423, wherein the transformer 1421 can be configured to provide an impedance-matched coupling between the second signal and the envelope detector. In an example, the second signal can include a voltage that can be detected between conductors in the implantable lead 1250, including a voltage that can include a phase-shifted version of the first signal. In this example, information indicative of lead motion can be realized by extracting a relatively low frequency component of a time-varying voltage from the second signal using the envelope detector 1423. In an example, the second signal comprises a large DC voltage with a small AC voltage superimposed, wherein the AC voltage can result from the response of the first signal to the modulated impedance. In an example, the implantable lead 1250 can be implanted in a heart and provided with the first signal. In this example, the resulting AC component of the second signal can include information about heart wall motion (or information indicative of one or more other mechanical vibrations coupled to the implantable lead 1250).

At 1850, information can be extracted from the demodulated second signal that can indicate motion of the implantable lead 1250. In an example, the second signal can be received from the implantable lead 1250. In an example, the second signal can be relatively constant over time (e.g., relatively constant in frequency or in amplitude, among other parameters) for a stationary or immobilized implantable lead 1250 because the impedance of the implantable lead 1250 can remain relatively unchanged at equilibrium. However, as the implantable lead 1250 undergoes movement (or as mechanical vibration is coupled to the lead), the movement of the implantable lead 1250 can modulate or change the impedance of the system containing the one or more conductors in the implantable lead 1250, and the second signal can deviate from its relatively constant amplitude or frequency. For example, a mechanical vibration coupled to the implantable lead 1250 can produce a microphonic effect such as receiving the vibration information by the implantable lead 1250 and providing a second signal in response to the first signal that is analogous to the received vibration. In this example, the mechanical vibration is effectively translated to an analogous electrical signal.

In an example, more than one implantable lead can be included in the ambulatory medical device 1400, as previously described. In this example, the first signal can be provided to the system comprising the multiple implantable leads and the second signal can be received from the same system. In an example, the relative or independent motion of the two or more leads can modulate the impedance of the system comprising the leads. In an example, the additional leads can provide a greater magnitude of impedance modulation of the system comprising the sensing elements, therefore exaggerating the response signal under some circumstances (e.g., using a "differential" measurement of multiple lead impedances or capacitances). Under some other set of circumstances, the impedance modulation of the system comprising the multiple sensing elements may have a nullifying effect on the response signal. In such an example, the implantable leads can be implanted or configured, or the conductors used for sensing can be selected, in such a manner as to create a specified response or sensitivity.

In an example, the demodulated signal can be provided to a signal processor 1430 for further extracting the information indicative of motion of the implantable lead 1250. In an example, the second signal can be high pass filtered to remove the low frequency wall motion and isolate higher frequency blood flow motion information. In this example, the pitch of the resulting signal can be related to the velocity of the blood flow. In an example, a demodulated and filtered signal can be transmitted, such as via an output 1440, to an external assembly, such as for visual or audible presentation to a clinician or care giver, such as using an audio amplifier. In an example, an examiner can listen to the blood flow information or the heart wall motion information provided by the medical device. For example, when the information indicative of motion includes a subsonic or ultrasonic component, such components can be respectively upconverted or downconverted (e.g., adjusted in speed or frequency) for playback using an audible range of frequencies.

Figure 19:
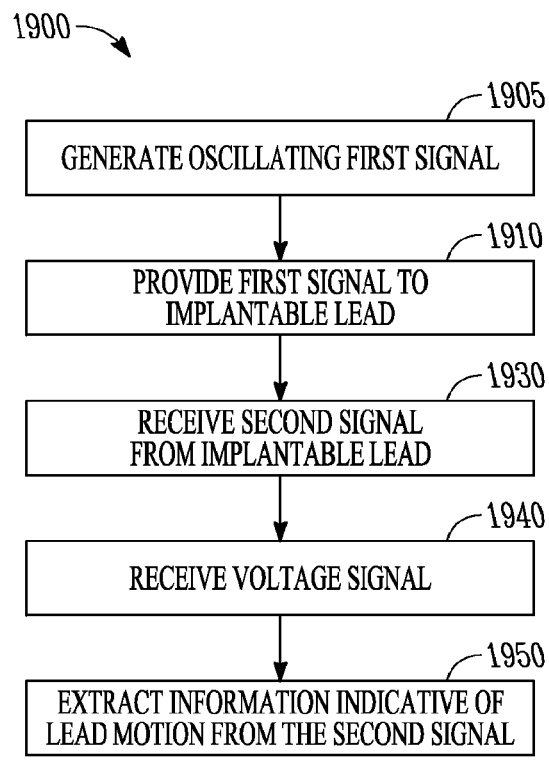
FIG. 19 illustrates generally an example of a portion of a method such as including generating an oscillating first signal, providing the first signal to an implantable lead, receiving a second signal from the implantable lead, receiving a voltage, or extracting information indicative of lead motion from the received voltage.

FIG. 19 illustrates generally an example 1900 that can include generating an oscillating first signal, providing the first signal to an implantable lead, receiving a second signal from the implantable lead, receiving a voltage signal, or extracting information indicative of lead motion from the voltage signal, such as using circuitry or techniques discussed above with respect to FIGS. 12-16.

At 1905, a first signal can be generated by an oscillator circuit included in excitation circuit 1210. In an example, the oscillator circuit can include a Pierce oscillator. In an example, the frequency of oscillation can in part determine the sensitivity of a system 1500. The frequency of the first signal can be specified to correspond to one or more frequencies that exhibit a change in impedance of an implantable lead 1250 at least in part due to motion of the implantable lead 1250.

At 1910, a first signal can be provided to the implantable lead 1250. In an example, the first signal can be an AC signal routed through a bridge circuit 1521. In this example, the implantable lead 1250 can form a portion (e.g., one of the legs) of the bridge circuit 1521. In an example, a capacitive element 1525 forms the leg of the bridge circuit 1521 that is opposite the implantable lead 1250. In an example, positive half cycles of the first signal can charge a first capacitance provided by the implantable lead 1250. In an example, the capacitive element 1525 can act as a second capacitance, which can be charged during negative half cycles of the first signal.

At 1930, a second signal can be received from the implantable lead 1250 wherein the second signal can be a response to the first signal. In an example, the second signal can be a voltage signal indicating a voltage across the first capacitance, and thus a change in capacitance of the implantable lead 1250 can be transformed into a voltage signal. The second signal can be a voltage signal indicating a voltage across the second capacitance.

At 1940, the voltage signal can be received. In an example, a voltage signal indicating a change in capacitance can be received by the envelope detector 1527. In an example, the envelope detector 1527 can be a diode or rectifier detector or a synchronous detector operating at the same frequency as the first signal. In an example, the voltage across the envelope detector 1527 can include a relatively constant value (e.g., amplitude or frequency) when the implantable lead 1250 is at equilibrium. However, when the capacitance of implantable lead 1250 changes, such as during a movement of the implantable lead 1250, the voltage across the envelope detector 1527 can change by an amount proportional to the displacement of the implantable lead 1250, the magnitude of the change in capacitance indicative of displacement.

At 1950, information can be extracted from the envelope detector 1527 that can be indicative of motion of the implantable lead 1250. In an example, a signal can be transmitted to an external source and amplified by an audio amplifier. In an example, an examiner can listen to heart sound information, as discussed above in the example of FIG. 18. In an example, heart wall motion information can be isolated and visually or audibly presented to the examiner (e.g., a clinician or caregiver).

Figure 20:
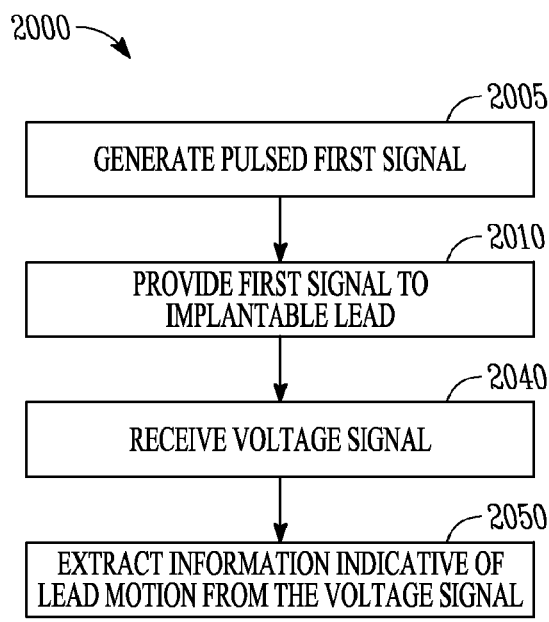
FIG. 20 illustrates generally an example that can include generating a pulsed first signal, providing the first signal to an implantable lead, receiving a voltage, or extracting information indicative of lead motion from the received voltage.

FIG. 20 illustrates generally an example 2000 that can include generating a pulsed first signal, providing the first signal to an implantable lead, receiving a voltage, or extracting information indicative of lead motion, such as using circuitry or techniques discussed above with respect to FIGS. 12-16.

At 2005, a first signal can be generated by a pulse generator. In an example, the pulse generator can produce a sequence of square wave pulses, or pulses having one or more other specified levels, duty cycles, repetition rates, or the like.

At 2010, a first signal can be provided to an implantable lead 1250. In an example, a first signal can be received from the excitation circuit 1610 by the detection circuit 1620. The received first signal can be coupled to the multiplexer 1621 in detection circuit 1620. In an example, the multiplexer 1621 can be coupled to the implantable lead 1250 via the interconnect 1660 and the lead coupling 1270. In an example, the detection circuit 1620 can include a multiplexer 1621 that can control the coupling of the first signal to the implantable lead 1250. The multiplexer 1621 can also be configured to apply a first signal to the capacitive element 1625.

At 2040, a voltage signal can be received. In an example, the multiplexer 1621 can be configured to apply a first signal to the implantable lead 1250 for a specified duration of time. In an example, the voltage signal can include a first voltage measurement of the implantable lead after a specified duration of time. In an example, the multiplexer 1621 can be configured to apply a first signal to the capacitive element 1625 for a specified duration of time (e.g., to charge the capacitive element 1625). The voltage signal can include a second voltage measurement of the capacitive element 1625 after a specified duration of time.

At 2050, information can be extracted from one or more of the first or second voltage signals indicative of motion of an implantable lead 1250. In an example, the voltage signal can be compared to a specified threshold voltage, or one or more voltage signals can be compared to an array of threshold voltages.

Figure 21:
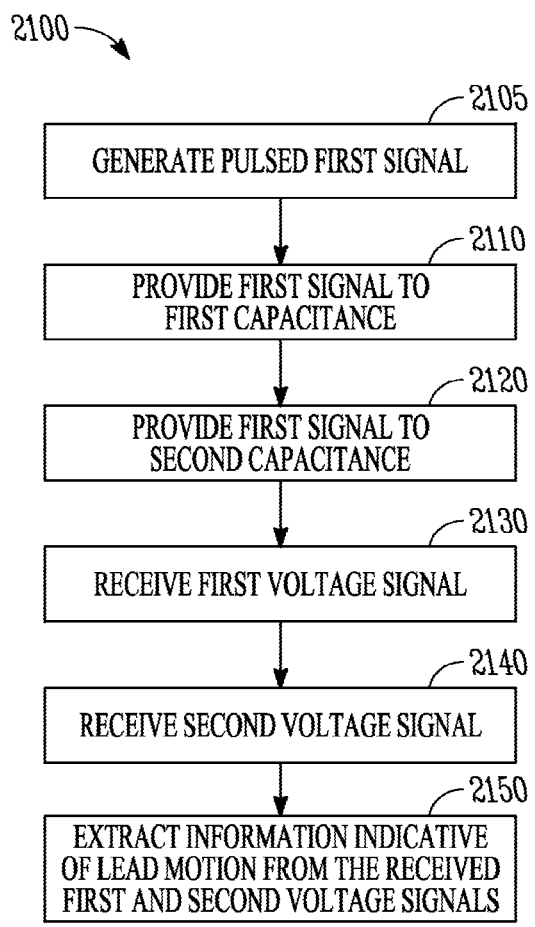
FIG. 21 illustrates generally an example that can include generating a pulsed first signal, providing the first signal to a first capacitance, providing the first signal to a second capacitance, receiving a first voltage, receiving a second voltage, or extracting information indicative of lead motion from the received first and second voltages.

FIG. 21 illustrates generally an example 2100 that can include generating a pulsed first signal, providing the pulsed first signal to a first capacitance, providing the pulsed first signal to a second capacitance, receiving a first voltage, receiving a second voltage, or extracting information indicative of lead motion.

At 2105, a first signal can be generated by a pulse generator. In an example, the pulse generator can produce pulses such as including one or more current or voltage pulses including pulses of a specified amplitude, duty cycle, or morphology, among other parameters.

At 2110, a first signal can be provided to a first capacitance. In an example, the first capacitance can be provided at least in part by the implantable lead 1250. In an example, the first signal can be received from the excitation circuit 1610 by the detection circuit 1620. The received first signal can be coupled to the multiplexer 1621 in the detection circuit 1620. The multiplexer 1621 can be coupled to the implantable lead 1250 via the interconnect 1660 and the lead coupling 1270. In an example, the detection circuit 1620 can operate the multiplexer 1621 to determine when a first signal can be applied to the implantable lead 1250.

At 2120, the first signal can be similarly provided to the second capacitance. For example, the second capacitance can be provided by the capacitive element 1625. In an example, the multiplexer 1621 can be coupled to the capacitive element 1625. In an example, the detection circuit 1620 can operate the multiplexer 1621 to controllably couple the first signal to the second capacitance. The capacitive element 1625 can be a discrete or distributed capacitor or a combination of capacitors providing a specified capacitance value, a second implantable lead, or an array of interconnected implantable leads or conductors, among others.

At 2130, a first voltage signal can be received. The first voltage signal can be a signal in response to the first signal. In an example, the first voltage signal can indicate, among other things, a charge level of the first capacitance or a first count of a number of pulses provided by the first signal.

At 2140, the second voltage signal can be received. The second voltage signal can be a signal in response to the first signal. In an example, the second voltage signal can indicate, among other things, a charge level of the second capacitance or a second count of a number of pulses provided by the first signal.

At 2150, information can be extracted from the first and second voltage signals indicative of motion of the implantable lead 1250. In an example, the first and second voltage signals can represent, respectively, a duration of respective first and second capacitor charge times. In this example, the first charge time can include an interval wherein the voltage across the first capacitance is between a lower voltage threshold and an upper voltage threshold. Similarly, the second charge time can include an interval wherein the voltage across the second capacitance is between the lower and upper voltage thresholds. In an example, information indicative of lead motion can be extracted by determining a relative indication of the first and second durations. For example, the first duration can be measured to be greater or lesser than the second duration. For example, the difference between the first and second durations can indicate the magnitude of the displacement of the implantable lead 1250, wherein the displacement causes a change in the first capacitance. In an example, when the first and second duration of a charge time are approximately equivalent, the relative indication of information can indicate that the implantable lead 1250 is stationary or otherwise at equilibrium. In an example, the first voltage signal can represent a first count of a number of pulses provided to the first capacitance. Similarly, the second voltage signal can represent a second count of a number of pulses provided to the second capacitance. In an example, information indicative of lead motion can be extracted by determining a relative indication of the first and second counts. For example, the difference between the first and second counts can indicate the magnitude of the displacement of the implantable lead 1250, wherein the displacement causes a change in the first capacitance. In an example, when the first and second counts are approximately equivalent or unchanging, the relative indication of information can indicate that the implantable lead 1250 is stationary or otherwise at equilibrium.

Figure 22:
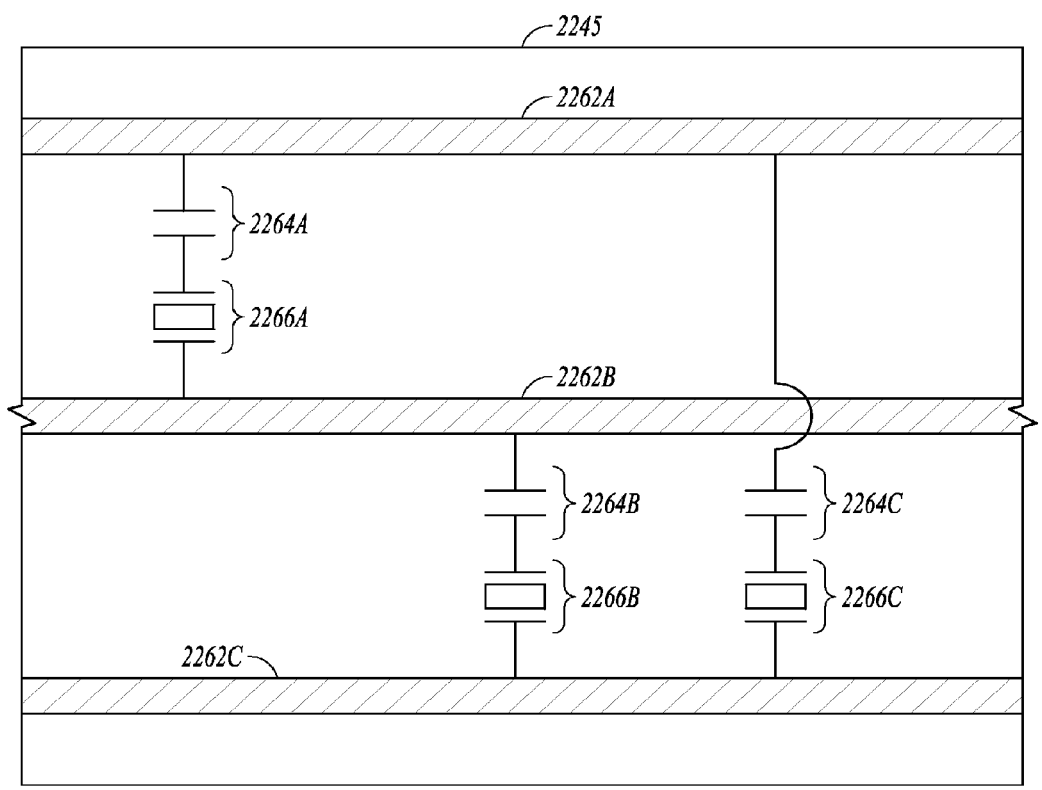
FIG. 22 illustrates generally an example of a portion of an implantable lead assembly that can include one or more transducers.

FIG. 22 illustrates generally an example of a portion of an implantable lead assembly 2245 that can include one or more piezoelectric transducers. In the example of FIG. 22, the implantable lead can include a first conductor 2262A, a second conductor 2262B, or a third conductor 2262C. A first transducer 2266A can be located on or within the lead assembly 2245, such as electrically coupled between the first conductor 2262A and the second conductor 2262B, such as including a first series capacitor 2264A (e.g., a DC-blocking capacitor). Similarly, a second transducer 2266B can be electrically coupled between the second conductor 2262B and the third conductor 2262C, such as via a second series capacitor 2264B. A third transducer 2266C can be electrically coupled between the first conductor 2262A and the third conductor 2262C, such as via a third series capacitor 2264C. Thus, in the example of FIG. 22, one or more of the transducers 2266A-C can be sampled or addressed via measurement or stimulation of a desired conductor pair (e.g., first and third conductors 2262A,C to address the third transducer 2266C, etc.).

In an example, one or more of the transducers 2266A-C can be excited such as to convert a non-therapeutic, non-stimulating electrical signal into acoustic energy (e.g., to provide acoustic energy such as ultrasonic energy). Conversely, one or more of the transducers 2266A-C can be configured for one or more of passive reception of acoustic energy (or mechanical vibration), or for reception of the acoustic transmission provided by another transducer, or the transducer being excited can modulate the excitation signal in response to received mechanical or acoustic energy. One or more of the conductors 2262A-C can be therapy delivery or cardiac electrical activity sensing conductors (e.g., the lead assembly 2245 need not carry extra conductors dedicated for use by the one or more transducers 2266A-C).

One or more of the transducers 2266A-C can include a piezoelectric construction, such as including metal or other conductive materials coupled to a lead-zirconate titanate material (PZT) piezoelectric material or coupled to a polyvinylidene fluoride (PVDF) piezoelectric material. For example, one or more of transducers 2266A-C can be used to measure blood velocity or other physiologic velocities relative to the transducer location, such as using a Doppler technique (e.g., a continuous-wave Doppler flow measurement). For example, a flow signal obtained using such techniques can include a high-frequency portion corresponding to the moving blood, a low frequency portion corresponding to heart wall motion, and a near-DC component such as corresponding to phase noise of an oscillator used to excite the transducer.

In an example, acoustic transmissions can be made between one of the transducers 2266A-C and another one of the transducers 2266A-C, such as to obtain information about a distance between various transducers 2266A-C. Such a distance can be determined via measurement of the time-delay between initiating an acoustic transmission at a first location and receiving a corresponding transmission at a second location. Thus, in the example of FIG. 22, such time-of-flight measurements can provide independent information about three different distances (e.g., between pairs of transducers 2266A-C, or between one or more of the transducers 2266A-C and another acoustic transmitter or receiver elsewhere), which can be tracked to reveal relative changes in displacement of portions of the implantable lead 2245. Multipath or other errors can be controlled or reduced such as by time-gating the received acoustic energy such as to capture the first (e.g., direct) or other desired time-of-flight between a desired transmit-receive transducer pair.

The selection of piezoelectric materials and operating frequency ranges can include considerations of size or mechanical flexibility, or directivity of resulting acoustic (e.g., ultrasonic) transmission or reception. For example, the frequency can be selected to be high enough that the corresponding acoustic wavelength is small with respect to the dimensions of the transducer, providing more omni-directional transmission or reception of acoustic energy.

In an example, the one or more transducers 2266A-C can be addressed using a frequency-selective technique. For example, a resonant device such as a thickness-mode PZT device can be excited with a burst of electrical energy corresponding to the PZT device's resonant frequency. Two or more transducers can be placed parallel to each other electrically, such as at specified locations along the implantable lead assembly 2245, such as including staggered or offset resonant frequencies, such as to provide spatially-addressable transducers that can be addressed using a desired frequency range corresponding to the resonant of a desired transducer at a specified location.

In an example, one or more of the transducers 2266A-C need not be resonant. For example, non-resonant PVDF transducers can be used interchangeably for transmission or reception of acoustic energy. In an example, a narrow-band PZT transmitting transducer can be used, and a broadband PVDF receiving transducer can be used. In this manner, the PVDF receiver need not be carefully matched or tuned to the PZT transmitter.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system comprising:
   an implantable medical device (IMD) including:
      a receiver circuit, configured to be electrically coupled to a conductor comprising a portion of an implantable lead, the receiver circuit configured to receive a response to an excitation signal applied to the conductor of the lead, the response modulated according to a change in an electrical characteristic of at least one conductor in the lead to provide information indicative of a movement of the implantable lead due at least in part to a motion of a heart; and
      a sensing circuit configured to obtain information indicative of cardiac electrical activity; and
   a processor circuit configured to construct a template representative of a contraction of the heart, the template constructed using the information indicative of the movement of the implantable lead due at least in part to the motion of the heart during the contraction, and using the information indicative of cardiac electrical activity sensed during the contraction.

2. The system of claim 1, wherein the processor circuit is configured to construct a composite template using information about multiple contractions.

3. The system of claim 1, wherein the processor circuit is configured to construct the template at least in part via relating the information indicative of the movement of the implantable lead sampled during a specified interval of time to cardiac electrical activity information sampled during a similar interval of time, wherein the template is a two-dimensional template.

4. The system of claim 3, wherein the processor circuit is configured to determine a contraction metric using the two-dimensional template.

5. The system of claim 4, wherein the processor circuit is configured to determine the contraction metric via estimating an area enclosed by a shape formed by plotting the information indicative of the movement of the implantable lead received during the contraction with respect to the information indicative of cardiac electrical activity sensed during the contraction.

6. The system of claim 4, wherein the processor circuit is configured to determine the contraction metric via estimating a spatial central tendency of a shape formed by plotting the information indicative of the movement of the implantable lead received during the contraction with respect to the information indicative of cardiac electrical activity sensed during the contraction.

7. The system of claim 4, wherein the processor circuit is configured to determine the contraction metric via estimating a spatial dispersion between a first template corresponding to a first cardiac contraction and a second template corresponding to a second cardiac contraction.

8. The system of claim 1, further comprising an implantable lead configured to be located within or near the heart, wherein the implantable lead comprises a piezoelectric acoustic transducer configured to receive acoustic information indicative of the movement of the implantable lead, the piezoelectric acoustic transducer coupled to the conductor included in the implantable lead.

9. The system of claim 1, wherein the IMD comprises an excitation circuit configured to provide the excitation signal as a non-tissue stimulating, non-therapeutic electrical excitation signal to the conductor of the implantable lead, the signal comprising a time-varying signal including a first range of frequencies.

10. The system of claim 9, wherein the information indicative of the movement of the implantable lead includes one or more of magnitude information, or phase information, corresponding to one or more frequencies included in the first range of frequencies, wherein the magnitude information, or phase information, is determined at least in part using the response to the excitation signal.

11. The system of claim 10, wherein the one or more of the magnitude information, or the phase information, includes a time-varying portion corresponding to the movement of the implantable lead.

12. The system of claim 1, wherein the IMD comprises the processor circuit.

13. The system of claim 1, further comprising the implantable lead including the conductor, the implantable lead configured to be located within or near the heart.

14. The system of claim 13, wherein the conductor comprises one or more of a cardiac therapy delivery conductor or a cardiac electrical activity sensing conductor, the conductor configured to be coupled to an implantable electrode included as a portion of the implantable lead.

15. The system of claim 13, further comprising a first lead located within or near a first location of the heart; and
   a second lead located within or near a second location of the heart.

16. A processor-readable medium comprising instructions that, when executed by the processor, cause the processor to:
   receive, using a receiver circuit, a response to an excitation signal applied to a conductor in an implantable lead, the response modulated according to a change in an electrical characteristic of the conductor in the lead to provide information indicative of the movement of the implantable lead, wherein the conductor is electrically coupled to the receiver circuit, the receiver circuit included as a portion of an implantable medical device (IMD), and the movement due at least in part to a motion of a heart;

obtain information indicative of cardiac electrical activity using a sensing circuit; and construct a template representative of a contraction of the heart, the template constructed using information indicative of the movement of the implantable lead due at least in part to the motion of the heart during the contraction, and using the information indicative of cardiac electrical activity sensed during the contraction.

17. The processor-readable medium of claim 16, wherein the instructions to construct the template include instructions to construct a two-dimensional template relating the information indicative of the lead movement sampled during a specified interval of time to the information indicative of cardiac electrical activity sampled during a similar interval of time.

18. The processor-readable medium of claim 16, wherein the processor-readable medium comprises instructions that, when executed by the processor, cause the processor to determine a contraction metric using the two dimensional template.

19. The processor-readable medium of claim 18, wherein the processor-readable medium comprises instructions that, when executed by the processor, cause the processor to determine the contraction metric via estimating an area enclosed by a shape formed by plotting the information indicative of the movement of the implantable lead received during the contraction with respect to the information indicative of cardiac electrical activity sensed during the contraction.

20. The processor-readable medium of claim 18, wherein the processor-readable medium comprises instructions that, when executed by the processor, cause the processor to determine the contraction metric via estimating a spatial central tendency of a shape formed by plotting the information indicative of the movement of the implantable lead received during the contraction with respect to the information indicative of cardiac electrical activity sensed during the contraction.

21. The processor-readable medium of claim 16, wherein the processor-readable medium comprises instructions that, when executed by the processor, cause the processor to determine a contraction metric via estimating a spatial dispersion between a first template corresponding to a first cardiac contraction and a second template corresponding to a second cardiac contraction.

22. A system, comprising:

means for receiving a response to an excitation signal applied to a conductor in an implantable lead, the response modulated according to a change in an electrical characteristic of the conductor in the lead to provide information indicative of movement of the implantable lead, the conductor electrically coupled to a receiver circuit, the receiver circuit included as a portion of an implantable medical device (IMD), and the movement due at least in part to a motion of a heart;

means for obtaining information indicative of cardiac electrical activity using a sensing circuit; and means for constructing a template representative of a contraction of the heart, the template constructed using the information indicative of the movement of the implantable lead due at least in part to the motion of the heart during the contraction, and using the information indicative of cardiac electrical activity sensed during the contraction.

* * * * *